US011131661B2

(12) United States Patent
Adzhubei et al.

(10) Patent No.: US 11,131,661 B2
(45) Date of Patent: Sep. 28, 2021

(54) COMPOUNDS INHIBITING NEF-CALNEXIN INTERACTION

(71) Applicant: THE GEORGE WASHINGTON UNIVERSITY, A CONGRESSIONALLY CHARTERED NOT-FOR-PROFIT CORPORATION, Washington, DC (US)

(72) Inventors: Alexei Adzhubei, Moscow (RU); Michael Bukrinsky, Potomac, MD (US); Ruth Hunegnaw, Arlington, VA (US)

(73) Assignee: THE GEORGE WASHINGTON UNIVERSITY, A CONGRESSIONALLY CHARTERED NOT-FOR-PROFIT CORPORATION, Washington, DC (US)

( * ) Notice: Subject to any disclaimer, the term of this patent is extended or adjusted under 35 U.S.C. 154(b) by 0 days.

(21) Appl. No.: 16/841,444

(22) Filed: Apr. 6, 2020

(65) Prior Publication Data
US 2020/0340977 A1    Oct. 29, 2020

Related U.S. Application Data

(62) Division of application No. 16/069,483, filed as application No. PCT/US2017/013236 on Jan. 12, 2017, now Pat. No. 10,684,274.

(60) Provisional application No. 62/277,720, filed on Jan. 12, 2016.

(51) Int. Cl.
| | | |
|---|---|---|
| *G01N 33/50* | (2006.01) | |
| *A61K 31/18* | (2006.01) | |
| *A61K 31/167* | (2006.01) | |
| *A61K 31/404* | (2006.01) | |
| *C07C 223/06* | (2006.01) | |
| *C07C 381/00* | (2006.01) | |
| *C07D 209/56* | (2006.01) | |

(52) U.S. Cl.
CPC ....... *G01N 33/5041* (2013.01); *A61K 31/167* (2013.01); *A61K 31/18* (2013.01); *A61K 31/404* (2013.01); *C07C 223/06* (2013.01); *C07C 381/00* (2013.01); *C07D 209/56* (2013.01); *G01N 33/502* (2013.01); *G01N 2333/163* (2013.01); *G01N 2333/4727* (2013.01); *G01N 2500/02* (2013.01)

(58) Field of Classification Search
CPC ............ G01N 33/5041; G01N 33/502; G01N 2333/163; G01N 2333/4727; G01N 2500/02; A61K 31/167; A61K 31/18; A61K 31/404; C07C 223/06; C07C 381/00; C07D 209/56

USPC ........................................................ 514/410
See application file for complete search history.

(56) References Cited

U.S. PATENT DOCUMENTS

| 6,750,253 B1 | 6/2004 | Ottosen et al. |
| 2008/0227099 A1 | 9/2008 | Lawn et al. |

OTHER PUBLICATIONS

Mujawar et al., "Human immunodeficiency virus impairs reverse cholesterol transport from macrophages," PLoS Biol, 4:e365 (2006).
Asztalos et al., "Circulating Nef induces dyslipidemia in simian immunodeficiency virus-infected macaques by suppressing cholesterol efflux", J Infect Dis, 202:614-623 (2010).
Dubrovsky et al., "Liver X receptor agonist inhibits HIV-1 replication and prevents HIV-induced reduction of plasma HDL in humanized mouse model of HIV infection", Biochem Biophys Res Commun, 419:95-98 (2012).
Cui et al., "HIV protein Nef causes dyslipidemia and formation of foam cells in mouse models of atherosclerosis", FASEB J, 28:2828-2839 (2014).
Jennelle et al., "HIV-1 protein Nef inhibits activity of ATP-binding cassette transporter A1 by targeting endoplasmic reticulum chaperone calnexin", J Biol Chem, 289:28870-28884 (Oct. 17, 2014).
Helenius et al., "Roles of N-linked glycans in the endoplasmic reticulum", Annu.Rev.Biochem., 73:1019-1049 (2004).
Tanaka et al., "Human ABCA1 contains a large amino-terminal extracellular domain homologous to an epitope of Sjogren's Syndrome", Biochem Biophys Res Commun, 283:1019-1025 (2001).
Pind et al., "Participation of the endoplasmic reticulum chaperone calnexin (p88, IP90) in the biogenesis of the cystic fibrosis transmembrane conductance regulator", J Biol Chem, 269:12784-12788 (1994).
Loo et al., "Prolonged association of temperature-sensitive mutants of human P-glycoprotein with calnexin during biogenesis", J Biol Chem, 269:28683-28689 (1994).
Okuhira et al., "Purification of ATP-binding cassette transporter A1 and associated binding proteins reveals the importance of beta1-syntrophin in cholesterol efflux", J Biol Chem, 280:39653-39664 (2005).
Chevet et al., "Phosphorylation by CK2 and MAPK enhances calnexin association with ribosomes", EMBO J, 18:3655-3666 (1999).

(Continued)

*Primary Examiner* — Kristin A Vajda
(74) *Attorney, Agent, or Firm* — Polsinelli LLP; Kory D. Christensen

(57) ABSTRACT

The invention relates to compounds and methods for restoring or preserving cholesterol efflux in a cell infected with Human Immunodeficiency Virus (HIV) by preventing or decreasing an interaction between Negative Regulatory Factor (Nef) protein and Calnexin protein, and methods for screening for such compounds.

9 Claims, 7 Drawing Sheets
Specification includes a Sequence Listing.

(56) References Cited

OTHER PUBLICATIONS

Schrag et al., "The Structure of calnexin, an ER chaperone involved in quality control of protein folding", Mol Cell, 8:633-644 (2001).
Roderick et al., "Cytosolic phosphorylation of calnexin controls intracellular Ca(2+) oscillations via an interaction with SERCA2b", J Cell Biol, 149:1235-1248 (2000).
Myhill et al., "The subcellular distribution of calnexin is mediated by PACS-2", Mol Biol Cell, 19:2777-2788 (2008).
Cameron et al., "Calnexin phosphorylation attenuates the release of partially misfolded alpha1-antitrypsin to the secretory pathway", J Biol Chem, 284:34570-34579 (2009).
Lynes et al., "Palmitoylated TMX and calnexin target to the mitochondria-associated membrane", EMBO J, 31:457-470 (2012).
Lynes et al., "Palmitoylation is the switch that assigns calnexin to quality control or ER Ca2+ signaling", J Cell Sci, 126:3893-3903 (2013).
Lakkaraju et al., "Palmitoylated calnexin is a key component of the ribosome-translocon complex", EMBO J, 31:1823-1835 (2012).
Ranki et al., "Expression kinetics and subcellular localization of HIV-1 regulatory proteins Nef, Tat and Rev in acutely and chronically infected lymphoid cell lines", Arch Virol, 139:365-378 (1994).
Grzesiek et al., "Refined solution structure and backbone dynamics of HIV-1 Nef", Protein Sci, 6:1248-1263 (1997).
Akgun et al., "Conformational transition of membrane-associated terminally acylated HIV-1 Nef", Structure, 21:1822-1833 (2013).
Jung et al., "Structure, dynamics, and Hck interaction of full-length HIV-1 Nef", Proteinss 79:1609-1622 (2011).
Grzesiek et al., "The solution structure of HIV-1 Nef reveals an unexpected fold and permits delineation of the binding surface for the SH3 domain of Hck tyrosine protein kinase", Nature Struct Biol, 3:340-345 (1996).
Singh et al., "A novel dimer-tetramer transition captured by the crystal structure of the HIV-1 Nef", PLoS One, 6: e26629 92011).
Celniker et al., "ConSurf: Using Evolutionary Data to Raise Testable Hypotheses about Protein Function", Isr J Chem, 53:199-206 (2013).
Aiken et al., "Nef induces CD4 endocytosis: requirement for a critical dileucine motif in the membrane-proximal CD4 cytoplasmic domain", Cell, 76:853-864 (1994).
Bentham et al., "Role of myristoylation and N-terminal basic residues in membrane association of the human immunodeficiency virus type 1 Nef protein", J Gen Virol, 87:563-571 (2006).
Cui et al., "HIV-1 Nef mobilizes lipid rafts in macrophages through a pathway that competes with ABCA1-dependent cholesterol efflux", J Lipid Res, 53:696-708 (2012).
Ko et al., "The crystal structure of the DNase domain of colicin E7 in complex with its inhibitor Im7 protein", Structure, 7:91-102 (1999).
Kleanthous et al., "Structural and mechanistic basis of immunity toward endonuclease colicins", Nature Struct Biol 6:243-252 (1999).
Wallis et al., "Protein-protein interactions in colicin E9 DNase-immunity protein complexes. 1. Diffusion-controlled association and femtomolar binding for the cognate complex", Biochemistry, 34:13743-13750 (1995).
Wallis et al., "Protein-protein interactions in colicin E9 DNase-immunity protein complexes. 2. Cognate and noncognate interactions that span the millimolar to femtomolar affinity range", Biochemistry 34:13751-13759 (1995).
Breuer et al., "Biochemical indication for myristoylation-dependent conformational changes in HIV-1 Nef", Biochemistry, 45:2339-2349 (2006).
Trott et al., "AutoDock Vina: improving the speed and accuracy of docking with a new scoring function, efficient optimization, and multithreading", J Comp Chem, 31:455-461 (2010).
Ramezani et al., "Stimulation of Liver X Receptor Has Potent Anti-HIV Effects in a Humanized Mouse Model of HIV Infection", J Pharmacol Exp Ther, 354:376-383 (2015).
Morrow et al., "Stimulation of the liver X receptor pathway inhibits HIV-1 replication via induction of ATP-binding cassette transporter A1", Mol Pharmacol, 78:215-225 (2010).
Myerson et al., "Management of lipid disorders in patients living with HIV", J Clin Pharmacol, 55:957-974 (2015).
Wang et al., "Increased cardiovascular disease risk in the HIV-positive population on ART: potential role of HIV-Nef and Tat", Cardiovasc Pathol, 24:279-282 (2015).
Waheed et al., "Lipids and membrane microdomains in HIV-1 replication", Virus Res, 143:162-176 (2009).
Lee et al., "UBC9-dependent association between calnexin and protein tyrosine phosphatase 1B (PTP1B) at the endoplasmic reticulum", J Biol Chem, 290:5725-5738 (2015).
Gerlach et al., "HIV-1 Nef membrane association depends on charge, curvature, composition and sequence", Nature Chem Biol, 6:46-53 (2010).
Giese et al., "Specific and distinct determinants mediate membrane binding and lipid raft incorporation of HIV-1(SF2)", Nef. Virology, 355:175-191 (2006).
Hussain et al., "A fruitful decade from 2005 to 2014 for anthraquinone patents", Exp Opin Ther Pat, 25:1053-1064 (2015).
Esposito et al., "New anthraquinone derivatives as inhibitors of the HIV-1 reverse transcriptase-associated ribonuclease H function", Chemotherapy, 58:299-307 (2012).
Molinari et al., "Contrasting functions of calreticulin and calnexin in glycoprotein folding and ER quality control", Mol Cell, 13:125-135 (2004).
Danilczyk et al., "Functional relationship between calreticulin, calnexin, and the endoplasmic reticulum luminal domain of calnexin", J Biol Chem, 275:13089-13097 (2000).
Hebert et al., "The number and location of glycans on influenza hemagglutinin determine folding and association with calnexin and calreticulin", J Cell Biol, 139:613-623 (1997).
Raney et al., "Reconstitution and molecular analysis of an active human immunodeficiency virus type 1 Nef/p21-activated kinase 2 complex", J Virol, 79:12732-12741 (2005).
Danilczyk et al., "The lectin chaperone calnexin utilizes polypeptide-based interactions to associate with many of its substrates in vivo", J Biol Chem, 276:25532-25540 (2001).
Hahn et al., "Identification and crystallization of a protease-resistant core of calnexin that retains biological activity", J Struct Biol, 123:260-264 (1998).
Soding et al., "The HHpred interactive server for protein homology detection and structure prediction", Nucleic Acids Res, 33:W244-248 (2005).
Roy et al., "I-TASSER: a unified platform for automated protein structure and function prediction" Nat Protoc, 5:725-738 (2010).
Pieper et al., "ModBase, a database of annotated comparative protein structure models and associated resources", Nucleic Acids Res, 42:D336-346 (2014).
Kelley et al., "Protein structure prediction on the Web: a case study using the Phyre server:", Nat Protoc, 4:363-371 (2009).
Kallberg et al., "Template-based protein structure modeling using the RaptorX web server", Nat Protoc, 7:1511-1522 (2012).
Pawlowski et al., "MetaMQAP: a meta-server for the quality assessment of protein models", BMC Bioinformatics, 9:403 (2008).
Berman et al., "The Protein Data Bank", Nucleic Acids Res, 28:235-242 (2000).
The UniProt Consortium, "UniProt: a hub for protein information", Nucleic Acids Res, 43:D204-D212 (2014).
Fernandez-Fuentes et al., "M4T: a comparative protein structure modeling server", Nucleic Acids Res, 35:W363-W368 (2007).
Biasini et al., "SWISS-MODEL: modelling protein tertiary and quaternary structure using evolutionary information", Nucleic Acids Res, 42:W252-W258 (2014).
Di Tommaso et al., "T-Coffee: a web server for the multiple sequence alignment of protein and RNA sequences using structural information and homology extension", Nucleic Acids Res, 39:W13-W17 (2011).
Kozakov et al., "Achieving reliability and high accuracy in automated protein docking: ClusPro, PIPER, SDU, and stability analysis in CAPRI rounds 13-19", Proteins, 78:3124-3130 (2010).

(56) References Cited

OTHER PUBLICATIONS

Ritchie et al., "Ultra-fast FFT protein docking on graphics processors", Bioinformatics, 26:2398-2405 (2010).
Torchala et al., "SwarmDock: a server for flexible protein-protein docking", Bioinformatics, 29:807-809 (2013).
Pierce et al., "ZDOCK server: interactive docking prediction of protein-protein complexes and symmetric multimers", Bioinformatics, 30:1771-1773 (2014).
Irwin et al., "ZINC—a free database of commercially available compounds for virtual screening", J Chem Info Model, 45:177-182 (2005).
Jubier-Maurin et al., "Genetic Characterization of the nef Gene from Human Immunodeficiency Virus Type 1 Group M Strains Representing Genetic Subtypes A, B, C, E, F, G, and H", AIDS Research and Human Retroviruses, vol. 15, No. 1, pp. 23-32 (1999).
Chemical Abstract compound, STN express. See RN 35106-31-1 (Entered STN: Nov. 16, 1984).
Chemcial Abstract compound, STN express. See RN 162331-05-7 (Entered STN: Apr. 20, 1995).
International Search Report from corresponding International Application No. PCT/US2017/013236, dated Jul. 20, 2017.
Written Opinion from corresponding International Application No. PCT/US2017/013236, dated Jul. 20, 2017.
Lord et al. J. Chem. Soc. (C), 1971.

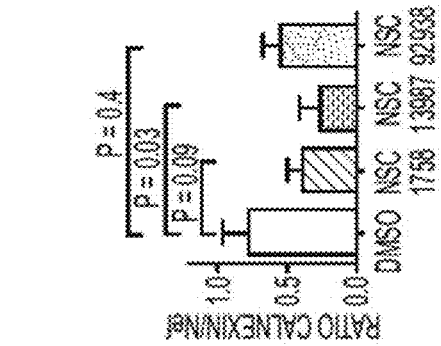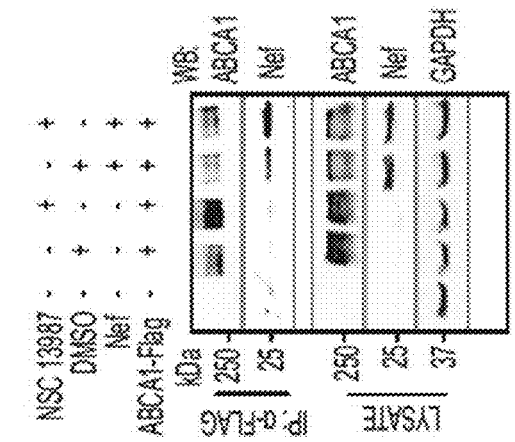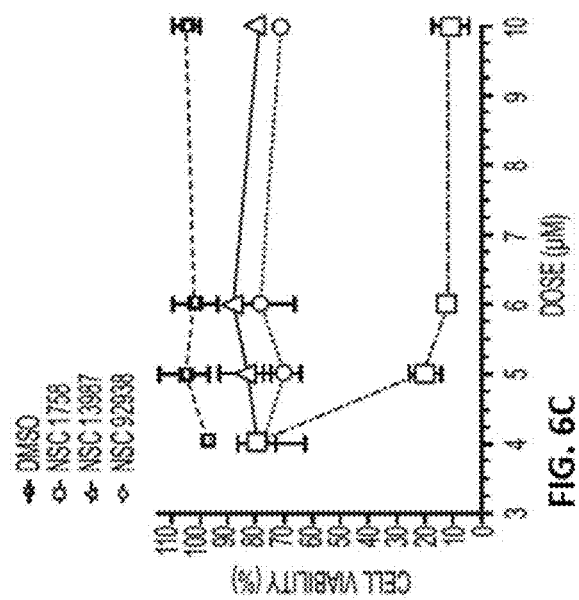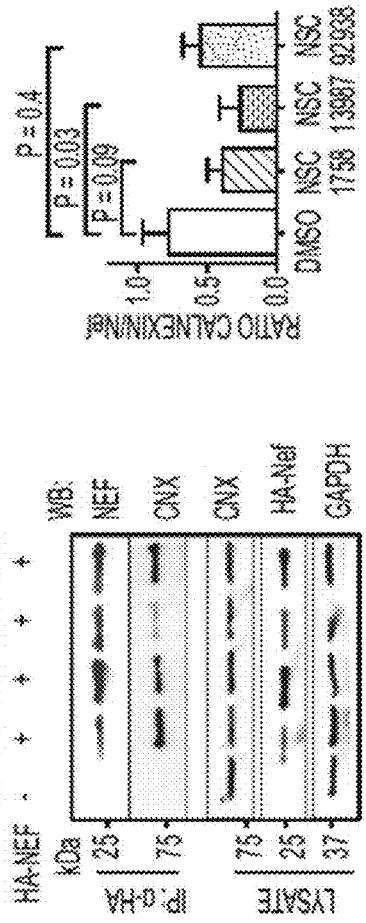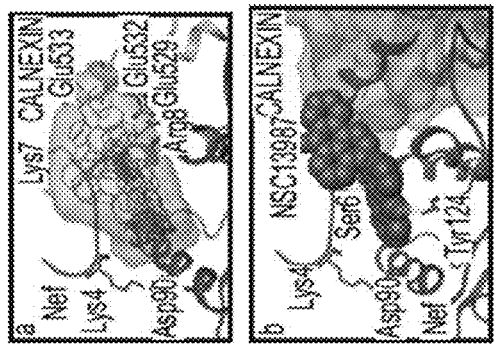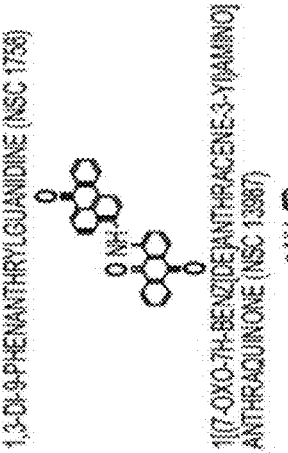

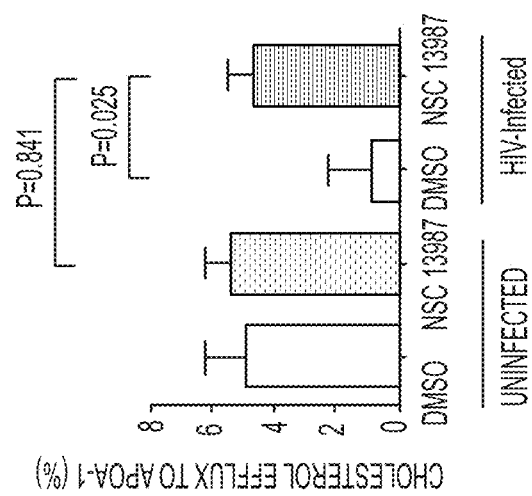
FIG. 7C
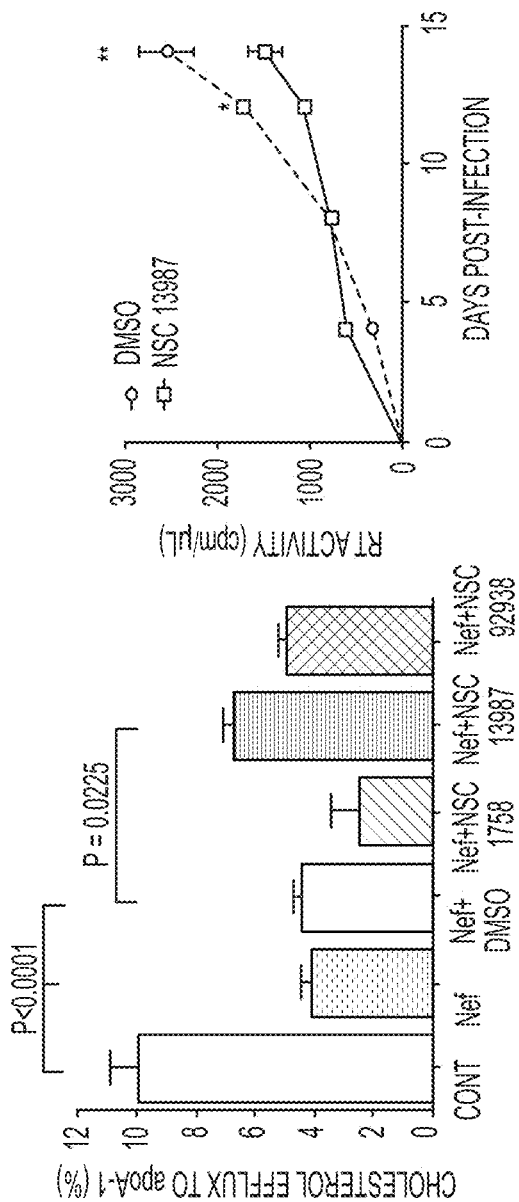
FIG. 7B
FIG. 7A

SEQUENCE LISTING

```
<160> NUMBER OF SEQ ID NOS: 12

<210> SEQ ID NO 1
<211> LENGTH: 6
<212> TYPE: PRT
<213> ORGANISM: Homo sapiens

<400> SEQUENCE: 1

Arg Lys Pro Arg Arg Glu
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 2

His His His His His His His His
1               5

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttgctataa gatgggtggc gcgtggtcaa aaagtagtgt gg                           42

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccacactact ttttgaccac gcgccaccca tcttatagca aa                           42

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gatgggtggc aagtggtcag caagtagtgt ggttggatgg                             40
```

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccatccaacc acactacttg ctgaccactt gccacccatc                              40

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggtggcgcg tggtcagcaa gtagtgtggt tgga                                   34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tccaaccaca ctacttgctg accacgcgcc accc                                   34

<210> SEQ ID NO 9
<211> LENGTH: 621
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgggtggca agtggtcaaa acgtagtgtg gttggatggc ctgctgtaag ggaaagaatg        60
agacgagctg agccagcagc agatgggggtg ggagcagtat ctcgagacct ggaaaaacat      120
ggagcaatca caagtagcaa tacagcagct aacaatgctg attgtgcctg gctagaagca      180
caagaggagg aggaggtggg ttttccagtc agacctcagg tacctttaag accaatgact      240
tacaaggcag ctgtagatct tagccacttt ttaaaagaaa agggggggact ggaagggcta      300 atttactccc aaaaaagaca agatatcctt gatctgtggg tctaccacac acaaggctac      360
ttccctgatt ggcagaacta cacaccaggg ccagggatca gatatccact gacctttgga      420
tggtgcttca agctagtacc agttgagcca gagaaggtag aagaggccaa tgaaggagag      480
aacaacagct tgttacaccc tatgagcctg catgggatgg atgacccgga gaaagaagtg      540
ttagtgtgga agtttgacag ccgcctagca tttcatcaca tggcccgaga gctgcatccg      600
gagtactaca aggactgctg a                                                621

<210> SEQ ID NO 10
<211> LENGTH: 206
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Met Gly Gly Lys Trp Ser Lys Arg Ser Val Val Gly Trp Pro Ala Val
1               5                   10                  15

Arg Glu Arg Met Arg Arg Ala Glu Pro Ala Ala Asp Gly Val Gly Ala
                20                  25                  30

Val Ser Arg Asp Leu Glu Lys His Gly Ala Ile Thr Ser Ser Asn Thr
            35                  40                  45

Ala Ala Asn Asn Ala Asp Cys Ala Trp Leu Glu Ala Gln Glu Glu Glu
        50                  55                  60

Glu Val Gly Phe Pro Val Arg Pro Gln Val Pro Leu Arg Pro Met Thr
65                  70                  75                  80

Tyr Lys Ala Ala Val Asp Leu Ser His Phe Leu Lys Glu Lys Gly Gly
                85                  90                  95

Leu Glu Gly Leu Ile Tyr Ser Gln Lys Arg Gln Asp Ile Leu Asp Leu
                100                 105                 110

Trp Val Tyr His Thr Gln Gly Tyr Phe Pro Asp Trp Gln Asn Tyr Thr
            115                 120                 125

Pro Gly Pro Gly Ile Arg Tyr Pro Leu Thr Phe Gly Trp Cys Phe Lys
        130                 135                 140

Leu Val Pro Val Glu Pro Glu Lys Val Glu Glu Ala Asn Glu Gly Glu
145                 150                 155                 160

Asn Asn Ser Leu Leu His Pro Met Ser Leu His Gly Met Asp Asp Pro
                165                 170                 175

Glu Lys Glu Val Leu Val Trp Lys Phe Asp Ser Arg Leu Ala Phe His
                180                 185                 190

His Met Ala Arg Glu Leu His Pro Glu Tyr Tyr Lys Asp Cys
            195                 200                 205
```

<210> SEQ ID NO 11
<211> LENGTH: 1779
<212> TYPE: DNA
<213> ORGANISM: Homo sapiens

<400> SEQUENCE: 11

```
atggaaggga agtggttgct gtgtatgtta ctggtgcttg gaactgctat tgttgaggct      60
catgatggac atgatgatga tgtgattgat attgaggatg accttgacga tgtcattgaa     120
gaggtagaag actcaaaacc agataccact gctcctcctt catctcccaa ggttacttac     180
aaagctccag ttccaacagg ggaagtatat tttgctgatt cttttgacag aggaactctg     240
tcagggtgga tttttatccaa agccaagaaa gacgataccg atgatgaaat tgccaaatat     300 gatgaaagt gggaggtaga ggaaatgaag gagtcaaagc ttccaggtga taaaggactt     360
gtgttgatgt ctcgggccaa gcatcatgcc atctctgcta aactgaacaa gcccttcctg     420
tttgacacca gcctctcat tgttcagtat gaggttaatt ccaaaatgg aatagaatgt      480 ggtggtgcct atgtgaaact gctttctaaa acaccagaac tcaacctgga tcagttccat     540
gacaagaccc cttatacgat tatgtttggt ccagataaat gtggagagga ctataaactg     600
cacttcatct tccgacacaa aaaccccaaa acgggtatct atgaagaaaa acatgctaag     660
aggccagatg cagatctgaa gacctatttt actgataaga aaacacatct ttacacacta     720
atcttgaatc cagataatag ttttgaaata ctggttgacc aatctgtggt gaatagtgga     780
aatctgctca atgacatgac tcctcctgta aatccttcac gtgaaattga ggacccagaa     840
```

```
gaccggaagc ccgaggattg ggatgaaaga ccaaaaatcc cagatccaga agctgtcaag      900
ccagatgact gggatgaaga tgcccctgct aagattccag atgaagaggc cacaaaaccc      960
gaaggctggt tagatgatga gcctgagtac gtacctgatc cagacgcaga gaaacctgag     1020
gattgggatg aagacatgga tggagaatgg gaggctcctc agattgccaa ccctagatgt     1080
gagtcagctc ctggatgtgg tgtctggcag cgacctgtga ttgacaaccc caattataaa     1140
ggcaaatgga agcctcctat gattgacaat cccagttacc agggaatctg aaacccagg     1200 aaaataccaa atccagattt cttttgaagat ctggaacctt tcagaatgac tcctttagt    1260 gctattggtt tggagctgtg gtccatgacc tctgacattt ttttgacaa ctttatcatt     1320 tgtgctgatc gaagaatagt tgatgattgg gccaatgatg gatggggcct gaagaaagct     1380
gctgatgggg ctgctgagcc aggcgttgtg gggcagatga tcgaggcagc tgaagagcgc     1440
ccgtggctgt gggtagtcta tattctaact gtagcccttc ctgtgttcct ggttatcctc     1500
ttctgctgtt ctggaaagaa acagaccagt ggtatggagt ataagaaaac tgatgcacct     1560
caaccggatg tgaaggaaga ggaagaagag aaggaagagg aaaaggacaa gggagatgag     1620
gaggaggaag gagaagagaa acttgaagag aaacagaaaa gtgatgctga agaagatggt     1680
ggcactgtca gtcaagagga ggaagacaga aaacctaaag cagaggagga tgaaattttg     1740
aacagatcac caagaaacag aaagccacga agagagtga                            1779
```

<210> SEQ ID NO 12
<211> LENGTH: 592
<212> TYPE: PRT
<213> ORGANISM: Homo sapiens

<400> SEQUENCE: 12

```
Met Glu Gly Lys Trp Leu Leu Cys Met Leu Leu Val Leu Gly Thr Ala
 1               5                  10                  15

Ile Val Glu Ala His Asp Gly His Asp Asp Asp Val Ile Asp Ile Glu
            20                  25                  30

Asp Asp Leu Asp Asp Val Ile Glu Glu Val Glu Asp Ser Lys Pro Asp
        35                  40                  45

Thr Thr Ala Pro Pro Ser Ser Pro Lys Val Thr Tyr Lys Ala Pro Val
    50                  55                  60

Pro Thr Gly Glu Val Tyr Phe Ala Asp Ser Phe Asp Arg Gly Thr Leu
65                  70                  75                  80

Ser Gly Trp Ile Leu Ser Lys Ala Lys Asp Asp Thr Asp Glu
                85                  90                  95

Ile Ala Lys Tyr Asp Gly Lys Trp Glu Val Glu Met Lys Glu Ser
            100                 105                 110

Lys Leu Pro Gly Asp Lys Gly Leu Val Leu Met Ser Arg Ala Lys His
        115                 120                 125

His Ala Ile Ser Ala Lys Leu Asn Lys Pro Phe Leu Phe Asp Thr Lys
    130                 135                 140

Pro Leu Ile Val Gln Tyr Glu Val Asn Phe Gln Asn Gly Ile Glu Cys
145                 150                 155                 160

Gly Gly Ala Tyr Val Lys Leu Leu Ser Lys Thr Pro Glu Leu Asn Leu
                165                 170                 175

Asp Gln Phe His Asp Lys Thr Pro Tyr Thr Ile Met Phe Gly Pro Asp
            180                 185                 190

Lys Cys Gly Glu Asp Tyr Lys Leu His Phe Ile Phe Arg His Lys Asn
        195                 200                 205
```

```
Pro Lys Thr Gly Ile Tyr Glu Glu Lys His Ala Lys Arg Pro Asp Ala
    210                 215                 220

Asp Leu Lys Thr Tyr Phe Thr Asp Lys Lys Thr His Leu Tyr Thr Leu
225                 230                 235                 240

Ile Leu Asn Pro Asp Asn Ser Phe Glu Ile Leu Val Asp Gln Ser Val
                245                 250                 255

Val Asn Ser Gly Asn Leu Leu Asn Asp Met Thr Pro Pro Val Asn Pro
            260                 265                 270

Ser Arg Glu Ile Glu Asp Pro Glu Asp Arg Lys Pro Glu Asp Trp Asp
        275                 280                 285

Glu Arg Pro Lys Ile Pro Asp Pro Glu Ala Val Lys Pro Asp Asp Trp
    290                 295                 300

Asp Glu Asp Ala Pro Ala Lys Ile Pro Asp Glu Glu Ala Thr Lys Pro
305                 310                 315                 320

Glu Gly Trp Leu Asp Asp Glu Pro Glu Tyr Val Pro Asp Pro Asp Ala
                325                 330                 335

Glu Lys Pro Glu Asp Trp Asp Glu Asp Met Asp Gly Glu Trp Glu Ala
            340                 345                 350

Pro Gln Ile Ala Asn Pro Arg Cys Glu Ser Ala Pro Gly Cys Gly Val
        355                 360                 365

Trp Gln Arg Pro Val Ile Asp Asn Pro Asn Tyr Lys Gly Lys Trp Lys
    370                 375                 380

Pro Pro Met Ile Asp Asn Pro Ser Tyr Gln Gly Ile Trp Lys Pro Arg
385                 390                 395                 400

Lys Ile Pro Asn Pro Asp Phe Phe Glu Asp Leu Glu Pro Phe Arg Met
                405                 410                 415

Thr Pro Phe Ser Ala Ile Gly Leu Glu Leu Trp Ser Met Thr Ser Asp
            420                 425                 430

Ile Phe Phe Asp Asn Phe Ile Ile Cys Ala Asp Arg Arg Ile Val Asp
        435                 440                 445

Asp Trp Ala Asn Asp Gly Trp Gly Leu Lys Lys Ala Ala Asp Gly Ala
    450                 455                 460

Ala Glu Pro Gly Val Val Gly Gln Met Ile Glu Ala Ala Glu Glu Arg
465                 470                 475                 480

Pro Trp Leu Trp Val Val Tyr Ile Leu Thr Val Ala Leu Pro Val Phe
                485                 490                 495

Leu Val Ile Leu Phe Cys Cys Ser Gly Lys Lys Gln Thr Ser Gly Met
            500                 505                 510

Glu Tyr Lys Lys Thr Asp Ala Pro Gln Pro Asp Val Lys Glu Glu Glu
        515                 520                 525

Glu Glu Lys Glu Glu Glu Lys Asp Lys Gly Asp Glu Glu Glu Glu Gly
    530                 535                 540

Glu Glu Lys Leu Glu Glu Lys Gln Lys Ser Asp Ala Glu Glu Asp Gly
545                 550                 555                 560

Gly Thr Val Ser Gln Glu Glu Asp Arg Lys Pro Lys Ala Glu Glu
                565                 570                 575

Asp Glu Ile Leu Asn Arg Ser Pro Arg Asn Arg Lys Pro Arg Arg Glu
            580                 585                 590
```

COMPOUNDS INHIBITING NEF-CALNEXIN INTERACTION

CROSS-REFERENCE OF RELATED APPLICATION

This application is a Divisional Application of U.S. patent application Ser. No. 16/069,483, filed on Jul. 11, 2018, which is a U.S. National Stage Application under 35 U.S.C. § 371 of PCT/US2017/013236, filed on Jan. 12, 2017, the entire content of which is hereby incorporated by reference, and claims priority to U.S. Provisional Application No. 62/277,720 filed Jan. 12, 2016; the entire contents of all of which are hereby incorporated by reference.

FEDERAL FUNDING BY U.S. GOVERNMENT

This invention was made with Government support under Grant Nos. R21 AI 14471, R01 HL101274 and R21 AI108533 each awarded by The National Institutes of Health (NIH). The U.S. Government has certain rights in the invention.

SEQUENCE LISTING

The instant application contains a Sequence Listing which has been filed electronically in ASCII format and is hereby incorporated by reference in its entirety. Said ASCII copy, created on Apr. 29, 2020, is named 123585_432794_SL.txt and is 12,499 bytes in size.

BACKGROUND

1. Technical Field

The field of the currently claimed embodiments of this invention relates to compounds and methods for restoring or preserving cholesterol efflux in a cell infected with Human Immunodeficiency Virus (HIV) by preventing or decreasing an interaction between Negative Regulatory Factor (Nef) protein and Calnexin protein, and methods for screening for such compounds.

2. Discussion of Related Art

Highly active anti-retroviral therapy (HAART) has transformed treatment of the HIV disease changing prognosis from acutely lethal to chronic illness, and lifespan of HIV-infected subjects approximates that of uninfected individuals. However, HAART does not cure HIV, and chronic HIV infection is associated with a number of co-morbidities, such as premature atherosclerosis and cardio-vascular disease (37). An essential component in pathogenesis of cardio-vascular disease in HIV-infected subjects is HIV-associated dyslipidemia, which is caused both by drugs used to treat HIV infection and by the effects of HIV itself on cholesterol metabolism (38).

HIV-1 infection, via activity of viral protein Nef, impairs cholesterol efflux mediated by the cholesterol transporter ATP-Binding Cassette A1 (ABCA1) (1). ABCA1 is the main cellular cholesterol transporter regulating delivery of cellular cholesterol to extracellular acceptor, apolipoprotein A-I. Studies in animal models demonstrated that this activity of Nef may be responsible for hypoalphalipoproteinemia and high risk of atherosclerosis observed in HIV-infected subjects (2-4). Recent studies identified calnexin, an integral endoplasmic reticulum (ER) membrane lectin-like chaperone, as a key player in the mechanism of Nef-mediated inhibition of ABCA1 and cholesterol efflux (5). Calnexin (CNX) and its homologue calreticulin (CRT) regulate folding and maturation of newly synthesized glycoproteins by engaging them in a CNX/CRT cycle (6).

ABCA1 is a highly glycosylated protein (7). Although no evidence for the role of CNX in ABCA1 biogenesis is available, two well-studied ABC transporters, ABCC7 (also known as cystic fibrosis transmembrane conductance regulator, CFTR) and ABCB1 (also known as multidrug resistance protein 1 or P-glycoprotein 1), interact with CNX, and folding mutants of these transporters are retained within the ER by CNX and eventually degraded (8, 9). Importantly, ABCC7 and ABCB1 mutants that escape CNX binding do not achieve mature glycosylation and these mutations result in reduced transporter function (8, 9). A recently published study demonstrated that ABCA1 interacts with CNX, and reduction of CNX expression by RNAi resulted in a significant decrease in functional activity of ABCA1, evidenced by reduced cholesterol efflux to ABCA1-specific acceptor apoA-I (5). It was also shown that Nef impairs interaction between ABCA1 and CNX, and this effect of Nef is essential for inactivation and downregulation of ABCA1 (5). Importantly, inhibition of ABCA1-calnexin interaction by Nef is specific, as interaction between ABCA1 and two other proteins, dystrophin and serine palmitoyltransferase, shown previously to bind ABCA1 (10), was not affected. Also not affected was the interaction between calnexin and HIV-1 envelope glycoprotein, gp160; in fact this interaction was even enhanced by Nef (5). These findings suggested that Nef modulates activity of calnexin, but the mechanism of this effect and molecular details of Nef/calnexin interaction remained unknown. Moreover, it was unclear whether the interaction between Nef and calnexin is direct, making screen for inhibitory compounds difficult.

Calnexin is a 592-amino acid Type I transmembrane protein composed of three parts: a lumenal fragment consisting of a globular β-sandwich domain responsible for the interaction with carbohydrates and a proline-rich tandem sequence repeat domain (the P domain) involved in protein-protein interactions, a transmembrane domain, and a cytoplasmic domain of 90 residues (11, 12). The cytoplasmic tail of calnexin can undergo phosphorylation and palmitoylation which regulate calnexin association with a number of proteins and protein complexes that influence functional activity of this chaperone (13-18). For example, palmitoylation of the C-tail of calnexin mediates its association with the ribosome-translocon complex, which is essential for the ability of calnexin to capture its client proteins as they emerge from the translocon (18). Ribosome association of calnexin is also regulated by phosphorylation on Ser534 and Ser544 by casein kinase 2 and on Ser563 by protein kinase C/proline-directed kinase (11). In addition, phosphorylation at Ser563 has been shown to play essential role in quality control function of calnexin (15). Therefore, the C-tail of calnexin may play a functional role regulating activity of the chaperone both directly, by affecting ER lumenal events involving calnexin, and indirectly, via modification of calnexin localization in the ER.

SUMMARY

An embodiment of the invention relates to a method for restoring or preserving cholesterol efflux in a cell infected with Human Immunodeficiency Virus (HIV) comprising delivering to the cell an effective amount of a composition or formulation comprising a small molecule. The small molecule prevents or decreases an interaction between a Negative Regulatory Factor (Nef) protein and a Calnexin protein.

Another embodiment of the invention relates to a method for treating or preventing atherosclerosis in a subject infected with HIV comprising administering to said subject an effective amount of a composition or formulation comprising a small molecule. The small molecule prevents or decreases an interaction between a Nef protein and a Calnexin protein.

Another embodiment of the invention relates to a method for screening for a small molecule that restores or preserves cholesterol efflux in a cell by inhibiting or decreasing an interaction between a Nef protein and a Calnexin protein including: incubating a cell expressing a full-length Nef protein or a segment of the full-length Nef protein and a full-length Calnexin protein or a segment of the full-length Calnexin protein with a small molecule of interest; assaying the incubated cell for cholesterol efflux; and assaying the incubated cell for a level of binding between the full-length Nef protein or the segment of the full-length Nef protein and the full-length Calnexin protein or the segment of the full-length Calnexin protein. In such embodiments, an increase in cholesterol efflux and a decrease in the level of binding as compared to a control is indicative of restoration or preservation of cholesterol efflux by inhibiting or decreasing an interaction between the Nef protein and the Calnexin protein as a result of incubation of the cell with the small molecule of interest.

An embodiment of the invention relates to a small molecule having the structure of Formula (I):

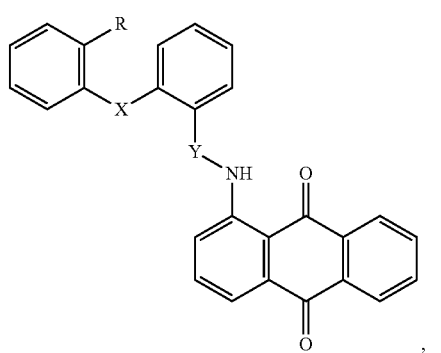

(I)

Where R is H, $CH_2OH$, COOH or $COOCH_3$; X is $CH_2$, NH, O, $NCH_3$, or $SO_2$; and Y is a bond, $CH_2$, CO or $SO_2$.

An embodiment of the invention relates to a small molecule having the structure of Formula (II):

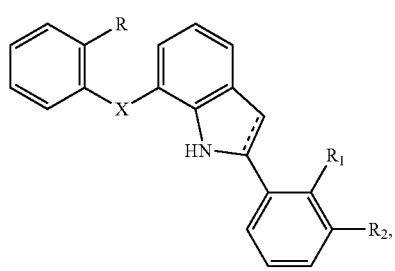

(II)

Where R, $R_1$, and $R_2$ are independently selected from H, $CH_2OH$, COOH or $COOCH_3$; and X is $CH_2$, NH, O, $NCH_3$, or $SO_2$.

An embodiment of the invention relates to a small molecule having the structure of Formula (III):

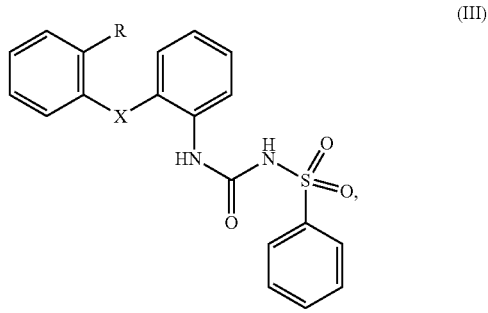

(III)

Where R is H, $CH_2OH$, COOH or $COOCH_3$; and X is $CH_2$, NH, O, $NCH_3$, or $SO_2$.

BRIEF DESCRIPTION OF THE DRAWINGS

Further objectives and advantages will become apparent from a consideration of the description, drawings, and examples.

FIG. 6A is a model showing where various small molecules disrupt the Nef and calnexin interaction;

FIG. 6B shows the structures of various small molecules according to some embodiments of the invention;

FIG. 6C is a graph showing the effects of various compounds on cell metabolism as a function of the dose;

FIG. 6D is a blot and bar graph showing the effects of several compounds ion Nef/CNX interaction;

FIG. 6E shows that the ABCA1/Nef interaction remains unaffected in the presence of the indicated compound;

FIG. 7A is a box graph showing cholesterol efflux as a function of treatment with various indicated compounds;

FIG. 7B is a graph showing a reduction in viral replication in response to the presence of the indicated compound; and FIG. 7C is a box graph showing that cholesterol efflux from HIV-infected cells was decreased by 60%, whereas HIV-infected cells treated with NSC 13987 showed cholesterol efflux not significantly different from that of mock-infected cells.

DETAILED DESCRIPTION

Figure 1B:
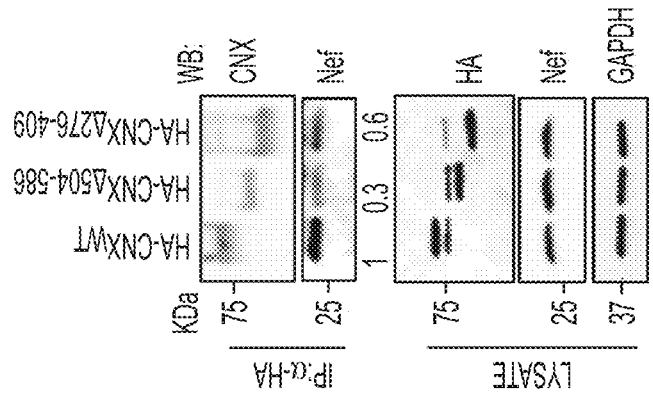
FIG. 1B is an immunoprecipitation assay showing expression of HA-tagged full-length and mutant calnexin constructs HEK293T cells.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Definitions

The abbreviations used throughout are: ABCA1, ATP-binding cassette A1; CNX, calnexin; CNX-CT, calnexin cytoplasmic tail; ER, endoplasmic reticulum; HA, hemagglutinin; HIV-1, human immunodeficiency virus type 1; HRP, horseradish peroxidase; PMA, phorbol-12-myristate 13-acetate; RT, reverse transcriptase.

As used throughout the phrase an "effective amount" of a composition of the invention is measured by the therapeutic effectiveness of a compound of the invention, wherein at least one adverse effect of a disorder is ameliorated or alleviated. More specifically, wherein administering a compound or composition results in restoration or preservation of cholesterol efflux in a cell or mammal infected with Human Immunodeficiency Virus (HIV).

As used herein and unless otherwise indicated, the term "formulation" refers to a composition comprising a compound of the invention that is described in a particular dosage form (e.g., tablet) or with a particular dosage amount (e.g., 30 mg/kg).

When administered to a subject (e.g., to an animal for veterinary use or to a human for clinical use), the compounds of the invention can be optionally administered in isolated form. As used herein, "isolated" means that the compounds of the invention are separated from other components of either (a) a natural source, such as a plant or cell, preferably bacterial culture, or (b) a synthetic organic chemical reaction mixture, preferably, via conventional techniques, the compounds of the invention are purified. As used herein, "purified" means that when isolated, the isolate contains at least 80% preferably at least 90%, more preferably at least 95%, and most preferably at least 99% of a compound of the invention by weight of the isolate.

The phrase "pharmaceutically acceptable salt(s)," as used herein includes but is not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds, included in the present compositions, that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein and unless otherwise indicated, the term "pharmaceutically acceptable prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise oligonucleotides, peptides, lipids, aliphatic and aromatic groups, or NO, $NO_2$, ONO, and $ONO_2$ moieties. Prodrugs can typically be prepared using well known methods, such as those described in Burger's Medicinal Chemistry and Drug Discovery, pp. 172, 178, 949, 982 (Manfred E. Wolff ed., 5th ed. 1995), and Design of Prodrugs (H. Bundgaard ed., Elselvier, N.Y. 1985).

The terms "treating or preventing" are intended to include preventing, eradicating, or inhibiting the resulting increase of undesired physiological activity associated with a disorder, for example, in the context of the therapeutic or prophylactic methods of the invention. In another embodiment, the term treating or preventing includes antagonistic effects, e.g., diminishment of the activity or production of mediators of a disorder.

An embodiment of the invention relates to a method for restoring or preserving cholesterol efflux in a cell infected with Human Immunodeficiency Virus (HIV) comprising delivering to the cell an effective amount of a composition or formulation comprising a small molecule. The small molecule prevents or decreases an interaction between a Negative Regulatory Factor (Nef) protein and a Calnexin protein.

Some embodiments of the invention relate to the method above, where the small molecule binds to at least one amino acid residue on the Nef protein. The at least one amino acid residue is selected from the group consisting of a lysine at amino acid position 4, a serine at amino acid position 6, a lysine at amino acid position 7, and a tyrosine at amino acid position 124.

Some embodiments of the invention relate to the method above, where the small molecule binds to at least one amino acid residue on the Calnexin protein. The at least one amino acid residue is selected from the group consisting of an aspartic acid at position 90, a glutamic acid at amino acid position 529, a glutamic acid at amino acid position 532, and a glutamic acid at amino acid position 533.

Some embodiments of the invention relate to the method above, where preventing or decreasing the interaction between the Nef protein and the Calnexin protein results in at least partial restoration of ATP-Binding Cassette A1 (ABCA1) activity.

Some embodiments of the invention relate to the method above, where the small molecule is a small molecule is selected from the group consisting of Formula (I), Formula (II), Formula (III) or an analog or derivative thereof:

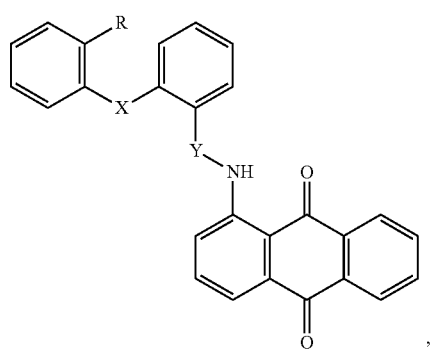

(I)

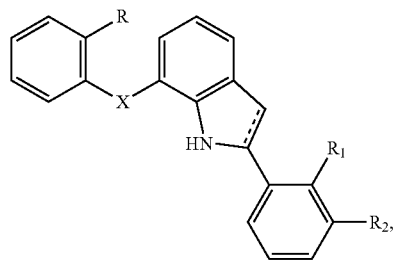

(II)

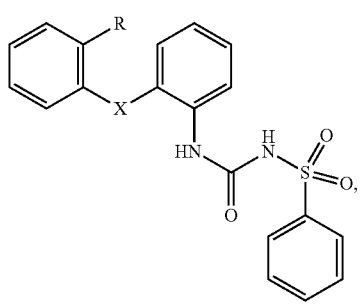

(III)

where R, $R_1$, and $R_2$ are independently selected from H, $CH_2OH$, COOH or $COOCH_3$; X is $CH_2$, NH, O, $NCH_3$, or $SO_2$; and Y is a bond, $CH_2$, CO or $SO_2$.

Some embodiments of the invention relate to the method above, where the small molecule is selected from the group consisting of Formula (IV), Formula (V), Formula (VI) or an analog or derivative thereof:

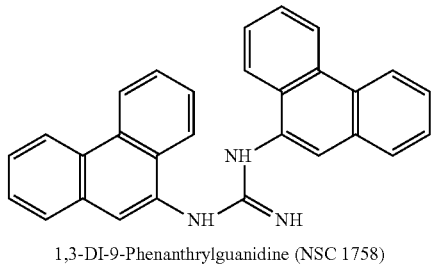

1,3-DI-9-Phenanthrylguanidine (NSC 1758)

(IV)

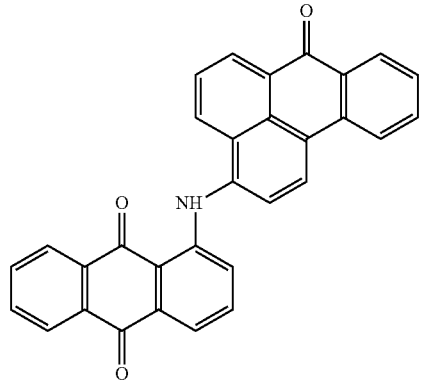

1[(7-Oxo-7H-benz[de]anthracene-3-yl)amino] anthraquinone (NSC 13987)

(V)

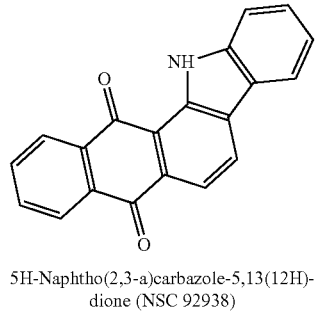

5H-Naphtho(2,3-a)carbazole-5,13(12H)-dione (NSC 92938)

(VI)

An embodiment of the invention relates to a method for treating or preventing atherosclerosis in a subject infected with HIV comprising administering to said subject an effective amount of a composition or formulation comprising a small molecule. The small molecule prevents or decreases an interaction between a Nef protein and a Calnexin protein.

Some embodiments of the invention relate to the method above, where the small molecule binds to at least one amino acid residue on the Nef protein. The at least one amino acid residue is selected from the group consisting of a lysine at amino acid position 4, a serine at amino acid position 6, a lysine at amino acid position 7, and a tyrosine at amino acid position 124.

Some embodiments of the invention relate to the method above, where the small molecule binds to at least one amino acid residue on the Calnexin protein. The at least one amino acid residue is selected from the group consisting of an aspartic acid at position 90, a glutamic acid at amino acid position 529, a glutamic acid at amino acid position 532, and a glutamic acid at amino acid position 533.

Some embodiments of the invention relate to the method above, where preventing or decreasing the interaction between the Nef protein and the Calnexin protein results in at least partial restoration of ATP-Binding Cassette A1 (ABCA1) activity.

Some embodiments of the invention relate to the method above, where the small molecule is a small molecule of Formula (I), Formula (II), or Formula (III), or an analog or derivative thereof.

An embodiment of the invention relates to a method for screening for a small molecule that restores or preserves cholesterol efflux in a cell by inhibiting or decreasing an interaction between a Nef protein and a Calnexin protein including: incubating a cell expressing a full-length Nef protein or a segment of the full-length Nef protein and a full-length Calnexin protein or a segment of the full-length Calnexin protein with a small molecule of interest; assaying the incubated cell for cholesterol efflux; and assaying the incubated cell for a level of binding between the full-length Nef protein or the segment of the full-length Nef protein and the full-length Calnexin protein or the segment of the full-length Calnexin protein. In such embodiments, an increase in cholesterol efflux and a decrease in the level of binding as compared to a control is indicative of restoration or preservation of cholesterol efflux by inhibiting or decreasing an interaction between the Nef protein and the Calnexin protein as a result of incubation of the cell with the small molecule of interest.

Some embodiments of the invention relate to the method above, further including a step of virtually screening a library of small molecules for a small molecule that is predicted to bind to or interact with at least one of the full-length Nef protein or the segment of the full-length Nef protein and the full-length Calnexin protein or the segment of the full-length Calnexin protein.

Some embodiments of the invention relate to the method above, where the cells are incubated for at least 1 day.

Some embodiments of the invention relate to the method above, where the assaying the incubated cell for a level of binding comprises an immunoprecipitation assay. In some embodiments, binding can be assayed with recombinant Nef and calnexin proteins using Surface Plasmon Resonance assay (Biacore) or Isothermal titration calorimetry.

An embodiment of the invention relates to a small molecule having the structure of Formula (I):

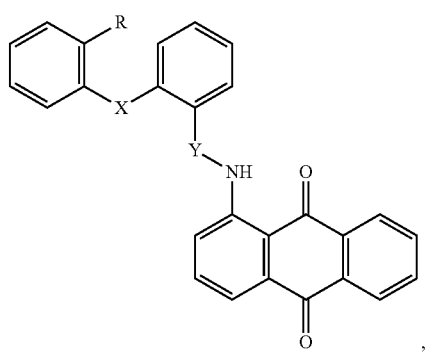

Where R is H, CH$_2$OH, COOH or COOCH$_3$; X is CH$_2$, NH, O, NCH$_3$, or SO$_2$; and Y is a bond, CH$_2$, CO or SO$_2$.

An embodiment of the invention relates to a small molecule having the structure of Formula (II):

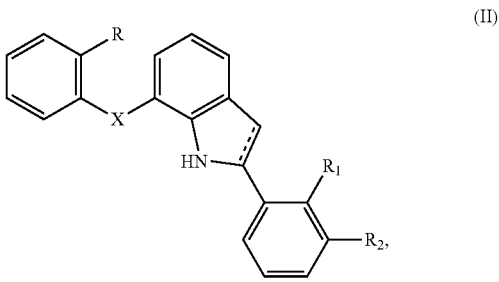

Where R, R$_1$, and R$_2$ are independently selected from H, CH$_2$OH, COOH or COOCH$_3$; and X is CH$_2$, NH, O, NCH$_3$, or SO$_2$.

An embodiment of the invention relates to a small molecule having the structure of Formula (III):

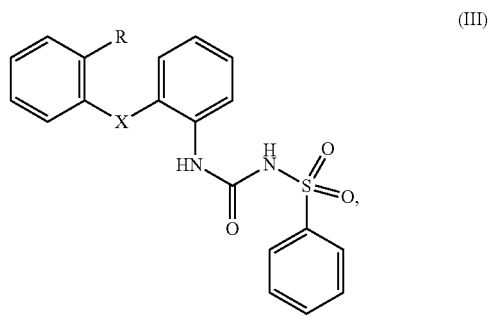

Where R is H, CH$_2$OH, COOH or COOCH$_3$; and X is CH$_2$, NH, O, NCH$_3$, or SO$_2$.

Some embodiments relate to combination therapeutic approaches where any of the methods and/or compounds described are combined with at least one other therapeutic agent or method for treating HIV. Common therapeutic agents include, but are not limited to: Nucleotide reverse transcriptase inhibitors; non-nucleotide RT inhibitors; integrate inhibitors; fusion inhibitors; protease inhibitors; and CCR5 inhibitors.

Some embodiments are compounds derived from the compounds of Formula (V). Such compounds include the compounds of Formulas (I), (II), and (III), for example. Considerations taken into account when modifying the chemical structure of Formula (V) to reach the chemical scaffolds of Formulas (I), (II) and (III) included the removal of the two aromatic rings and addition of functional groups that would improve the solubility of Formula (V) derivatives in aqueous media. More specifically, in some embodiments, the aromatic rings would be replaced with hydrophilic moieties to promote solubility in aqueous media and promote binding to Nef.

A first scaffold for Formula (V) derivatives includes changes to the tetracyclic core (Anthraquinone derivatives) as shown in Formula (I):

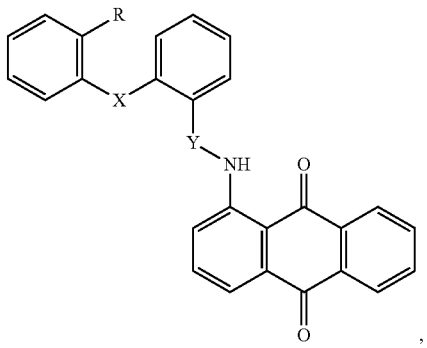

(I)

Where R is H, CH$_2$OH, COOH or COOCH$_3$; X is CH$_2$, NH, O, NCH$_3$, or SO$_2$; and Y is a bond, CH$_2$, CO or SO$_2$.

A second scaffold for Formula (V) derivatives includes changes to the tricyclic core (Indole/sulfonylurea derivatives) as shown in Formulas (II) and (III):

Formula (II):

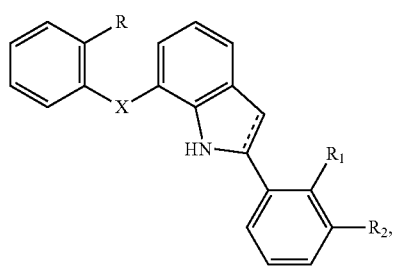

(II)

Where R, R$_1$, and R$_2$ are independently selected from H, CH$_2$OH, COOH or COOCH$_3$; and X is CH$_2$, NH, O, NCH$_3$, or SO$_2$.

Formula (III):

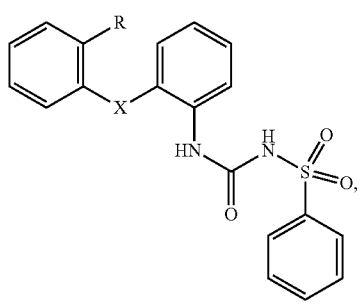

(III)

Where R is H, CH$_2$OH, COOH or COOCH$_3$; and X is CH$_2$, NH, O, NCH$_3$, or SO$_2$.

Example

In the following example, it is demonstrated that the C-tail of calnexin is targeted by the HIV-1 protein Nef, which uses this interaction to disrupt calnexin-assisted maturation of ABCA1 and impair cholesterol efflux. Important structural features of the Nef/calnexin interaction are characterized and a small molecule compound that blocks this interaction and reverses negative effects of HIV infection on cellular cholesterol metabolism is identified.

Results

Cytoplasmic Domain of Calnexin is Necessary for Interaction with Nef

Figure 1A:
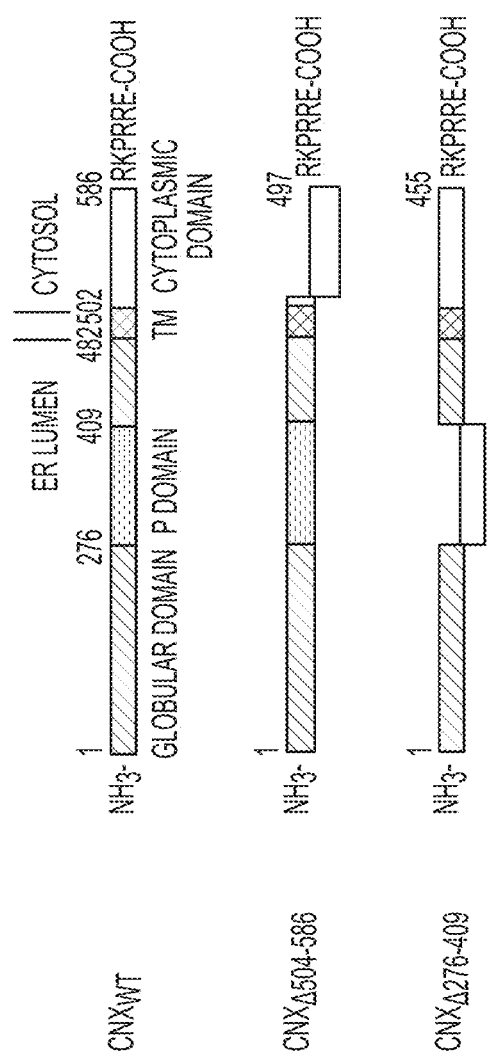
FIG. 1A shows a schematic of HA-tagged full-length and mutant calnexin constructs expressed in HEK293T cells ("RKPRRE" is disclosed as SEQ ID NO: 1)

In a previous study it was shown that HIV-1 Nef interacts with the ER chaperone calnexin (5). To test which region of calnexin is necessary for binding to Nef, calnexin constructs that had deletion of the lumenal repeat segment (aa 276-409) or truncation of the C-terminal cytoplasmic domain (aa 504-586) (FIG. 1A). HEK293T cells were transfected with Nef$_{BRU}$-expressing vector and HA-tagged variants of wild-type (WT) calnexin or the deletion mutants and performed co-immunoprecipitation. FIG. 1B shows that WT calnexin interacted strongly with Nef, whereas calnexin construct with internal repeat motif deletion (CNX$_{\Delta 276-409}$) exhibited binding reduced by 40%. However, binding of Nef to calnexin construct carrying the truncation of the C-terminal cytoplasmic tail (CMX$_{\Delta 504-586}$) was reduced by 70%. This finding highlights the importance of the cytoplasmic region of calnexin in interaction with Nef. The role of calnexin cytoplasmic tail in the interaction with Nef is consistent with Nef's localization to the cytoplasm (19). Of note, the cytoplasmic domain of calnexin is composed mainly of negatively charged amino acids, whereas the N-terminal region of Nef is enriched in positively charged residues. The modest effect that deletions in the lumenal repeat motif of calnexin have on Nef binding may be due to conformational changes, which could affect all domains of calnexin.

FIG. 1 shows a schematic of HA-tagged full-length and mutant calnexin constructs expressed in HEK293T cells and immunoprecipitation results of such constructs. Specifically, Panel (A) shows HA-tagged full-length and mutant calnexin constructs expressed in HEK293T cells. The various segments represented are the globular domain, tandem repeat motif, TM domain and C-terminal cytoplasmic tail, respectively. Dropped boxes represent deleted fragments. CNX$_{WT}$ represents full length calnexin, CNX$_{\Delta 486-567}$ has 81 out of the 89 cytoplasmic tail residues deleted while maintaining the ER localization sequence RKPRRE (SEQ ID NO: 1); CNX$_{\Delta 257-388}$ construct has 131 residues of the P domain deleted. In panel (B) HEK293T cells were co-transfected with Nef and HA-tagged CNX$_{WT}$, CNX$_{\Delta 486-567}$ or CNX$_{\Delta 257-388}$ vectors and blotted for HA, Nef and GAPDH (lysate). Calnexin variants were immunoprecipitated 48 h post-transfection using anti-HA coupled agarose beads and resulting immunoprecipitates were immunoblotted for Nef (upper panel). Numbers under the lanes show relative amounts of co-precipitated Nef obtained by gel densitometry.

Computational Model of Nef-CNX Interaction

Figure 2B:
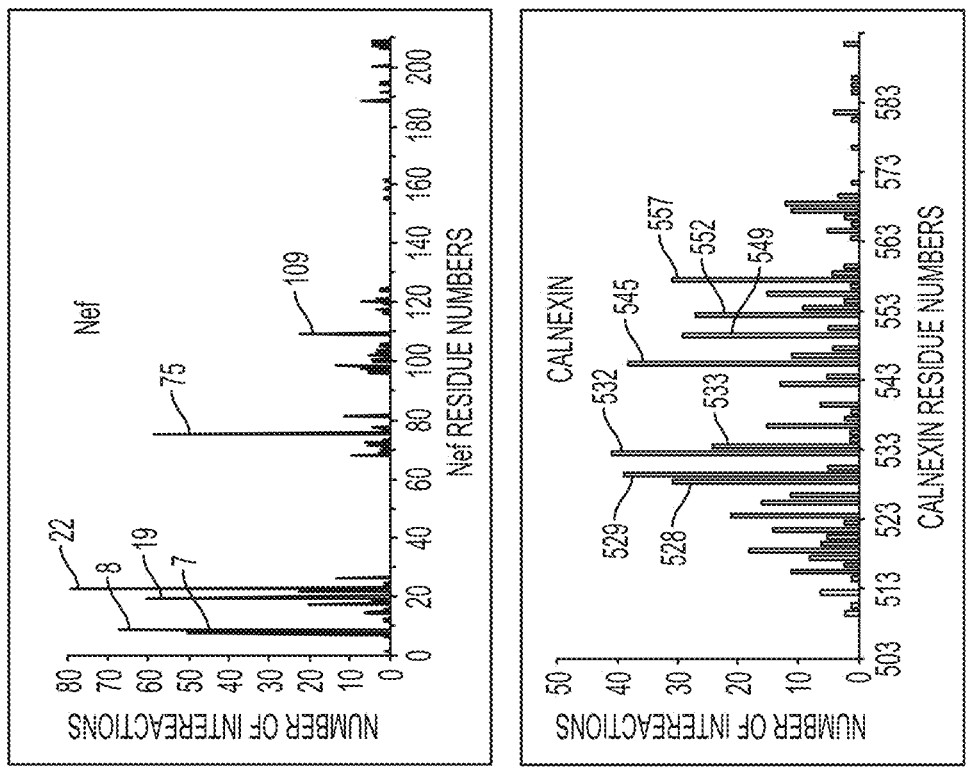
FIG. 2B shows interactions in Nef-CNX docking models mapped on Nef and calnexin sequences.
Figure 2A:
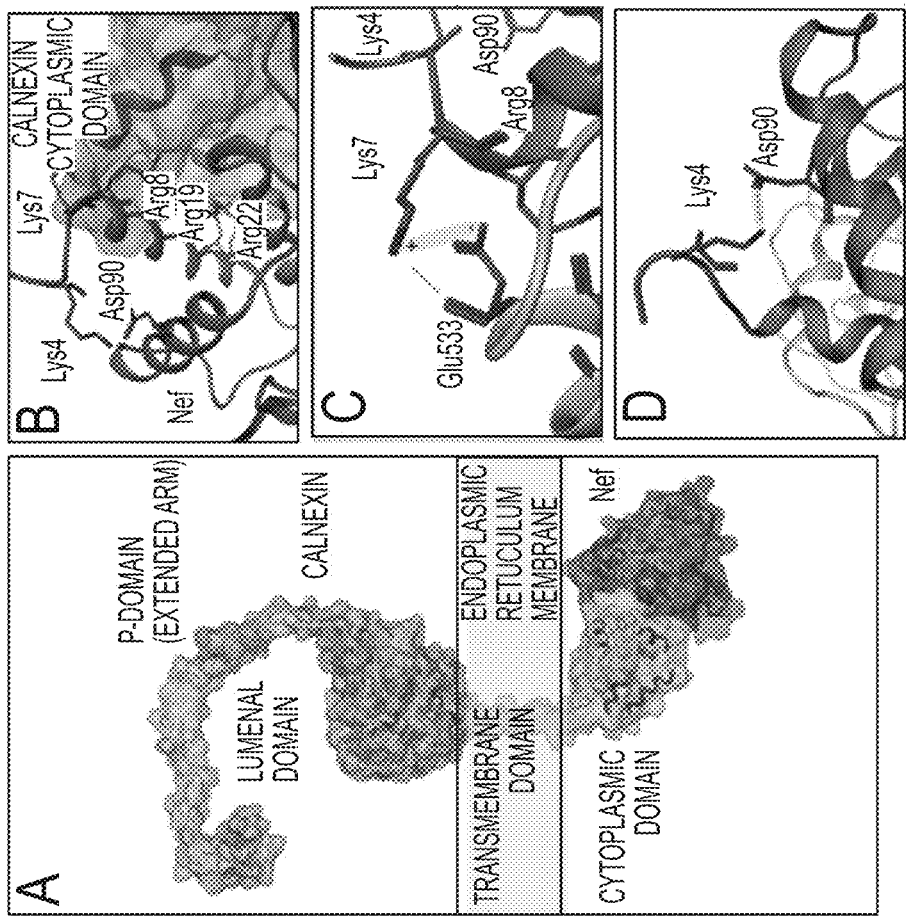
FIG. 2A shows representative models of Nef-CNX binding.

Experimentally solved molecular structure of calnexin is available only for the lumenal domain (12), and to obtain three-dimensional structure of calnexin cytoplasmic domain a modeling with several modeling servers implementing different methods was performed, which produced a number of models ranging from the fully folded structures to structures that included natively disordered regions. The models have been assessed for accuracy and final round of modeling performed with the server QA-RecombineIt. The final model had a loosely folded structure (FIG. 2A, panel a). Computational prediction of Nef-CNX complexes showed Nef N-terminal alpha-helix forming the interaction interface with calnexin cytoplasmic domain (FIG. 2A, panels b and c).

In comparison with the calnexin cytoplasmic domain model, the model of Nef was based on a number of experimental structures (20-24) and thus had better accuracy. Nef-CNX interaction has been modeled by global docking using four different docking servers, Cluspro, HEX, SwarmDock, and Zdock. Combined set of the best Nef-CNX docking models produced with these servers contained 80 models. The advantage of this approach is that the resulting models represented Nef-CNX interaction modeled by four different, unrelated methods and therefore it was more reliable than using a single server. From these, 49 models have been filtered out as possibly interfering with interaction of Nef with ER membrane. Intermolecular interactions in the remaining subset of 31 models have been identified. There are several distinct clusters of interactions, with sharp maxima for Lys7 and Arg in positions 8, 19, 22, 75 and 109 (FIG. 2B). Notably, similar analysis of interactions carried out on the full initial dataset of 80 docking models showed similar clustering and maxima (not shown). It can therefore be hypothesized that the identified residues represent the overall favorable Nef-CNX interaction sites. All these residues, except Lys7 and Arg8, have been also identified as participating in interactions in the experimental structures of complexes which included Nef. A representative model of Nef-CNX binding is shown in FIG. 2A, panels b and c. Analysis of the conserved residues in Nef performed with ConSurf (25) revealed several such conserved positions in the N-terminal region, including Lys4, Ser6, Lys7 and Arg19. Multiple sequence alignment of the human HIV Nef sequences from Uniprot showed that Lys7 is highly conserved across the spectrum of HIV-1 and HIV-2 sequences. Conserved residues indicate structurally and functionally important positions, including interaction sites. Therefore, Lys7 represents a new interaction site which was not previously identified in Nef interactions with other proteins.

FIG. 2 shows a schematic representation of Nef-CNX binding and the interactions in Nef-CNX docking models mapped on Nef and calnexin sequences. Specifically, panel (A) shows schematic representation of Nef-CNX binding. (a) Schematic representation of the calnexin structure. Lumenal domain is represented by the model structure; the transmembrane region is shown as a helical domain according to the Uniprot (calnexin, P27824) domain classification. Calnexin cytoplasmic domain and Nef are represented by models built as described in Experimental Procedures, and Nef/CNX binding is shown according to the results of docking. (b) Docking model of the CNX cytoplasmic domain (green)—Nef (magenta) interaction. The binding interface is formed by the Nef N-terminal alpha-helix, with Lys 7 and Arg 8, 19, and 22 forming interactions with CNX. (c) Lys7 in Nef (magenta) displays strong interaction with Glu533 in CNX (green) formed by the hydrogen and ionic bonds. (d) Lys4 plays a key role in the N-terminal region of Nef structure model (magenta). It forms a strong intramolecular interaction with Nef Asp90 with hydrogen and ionic bonds, supporting structural rigidity of the Nef N-terminal alpha-helix relative to the rest of Nef structure. Panel (B) shows interactions in Nef-CNX docking models mapped on Nef and calnexin sequences. Bars show the number of interactions, with the numbers for each maximum showing sequence number. In the Nef sequence, there are three distinct interaction clusters centered on residues 7, 22, 75 and 109, with sharp maxima for lysine 7, and arginines in positions 8, 19, 22, 75 and 109. Two interaction clusters in the calnexin sequence are formed by amino acids 528-533 and 545-557; they include glutamic acid residues in positions 529, 532, 533.

Lysine Residues of Nef in Positions 4 and 7 are Critical for Nef-CNX Interaction According to docking modeling and sequence conservation results, Lys7 possibly represents a new binding site in Nef and accordingly it has been selected for mutagenesis experiments. Lys4 has been also selected since it is a Lys7 near neighbor and, as demonstrated in the Nef model, it plays a key structural role for the N-terminus (FIG. 2A, panel d). Therefore, mutation of both Lys4 and Lys7 was predicted to invoke structural rearrangement in the Nef N-terminal region thus disrupting the interaction between Nef and calnexin. Alanine substitution of basic residues at the N-terminus of Nef has previously been shown to preserve membrane association and CD4 down-regulation by Nef (26), and intracellular localization of the mutant Nef was indistinguishable from that of Nef WT (27).

Figure 3A:
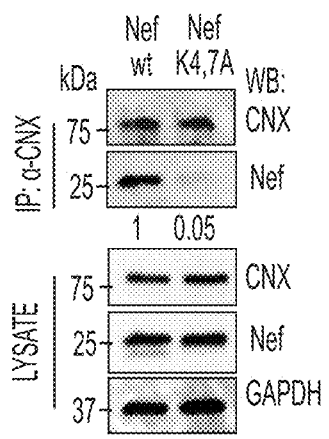
FIG. 3A shows immunoprecipitation results comparing the interaction between Nef Wild Type and Calnexin and NefK4,7A and Calnexin.

To verify the role of these residues in Nef interaction with calnexin, the mutant HIV-1 NL4-3 clone carrying Nef with Lys4 and Lys7 changed to alanines was used. Calnexin was immunoprecipitated from HEK293T cells transfected with WT or mutant HIV-1 clones and the precipitate was immunoblotted for Nef. As shown in FIG. 3A, interaction with calnexin was evident for Nef WT, but not for NefK4,7A. Interaction with the double mutant was reduced by 95%, indicating that the lysine residues in positions 4 and 7 are essential for Nef interaction with calnexin.

Figure 3B:
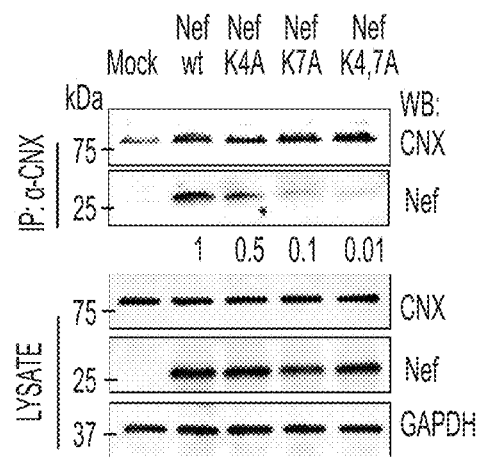
FIG. 3B shows immunoprecipitation results comparing the interaction between Nef Wild Type and Calnexin and various Nef mutants and Calnexin.
Figure 3C:
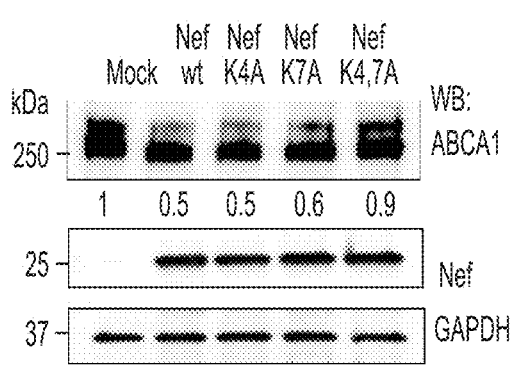
FIG. 3C shows ABCA1 abundance as a function of mutations to Nef.

In order to look at the individual contribution of the two lysine residues to the interaction with calnexin, the Nef$_{BRU}$ plasmid was mutagenized to create single and double lysine mutant constructs. HEK293T cells were transfected with WT or mutant Nef constructs and the amount of Nef found to immunoprecipitate with calnexin was analyzed again. Based on densitometric analysis, interaction of CNX with NefK4A was reduced by 50% whereas interaction with NefK7A was reduced by as much as 90% as compared to interaction with WT Nef (FIG. 3B). Interaction of calnexin with NefK4,7A was undetectable. This result was consistent with FIG. 3C, where the expression of ABCA1 in the presence of single Nef mutants as compared to the double lysine mutant was evaluated. NefK4A and NefK7A mutants reduced ABCA1 abundance as much as the wild-type Nef, whereas near control level of ABCA1 was observed when both lysine residues were mutated (FIG. 3C). This result highlights the importance of both residues in ABCA1 down-regulation, and suggests that even reduced interaction with calnexin observed for NefK4A and NefK7A mutants is sufficient for ABCA1 downregulation.

Figure 3D:
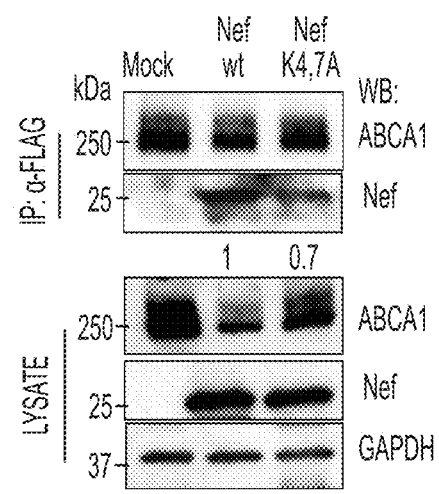
FIG. 3D shows NefK4,7A interaction with ABCA1 as compared to ABCA1 interaction with wild-type Nef.

To rule out the possibility that mutation of these residues grossly affected the behavior of the N-terminal domain of Nef, the interaction of the mutant Nef with ABCA1 was tested. Previous studies demonstrated that interaction between Nef and ABCA1 also involves the N-terminal domain (1), although the specific residues involved have not been identified. Co-precipitation analysis revealed about a 30% reduction in NefK4,7A interaction with ABCA1 as compared to ABCA1 interaction with wild-type Nef (FIG. 3D). The reduction, however, remains in stark contrast to the >95% loss of interaction observed in the Nef-CNX interaction studies (FIG. 3A).

Functional Analysis of Nef Mutants

Figures 4A, 4B:
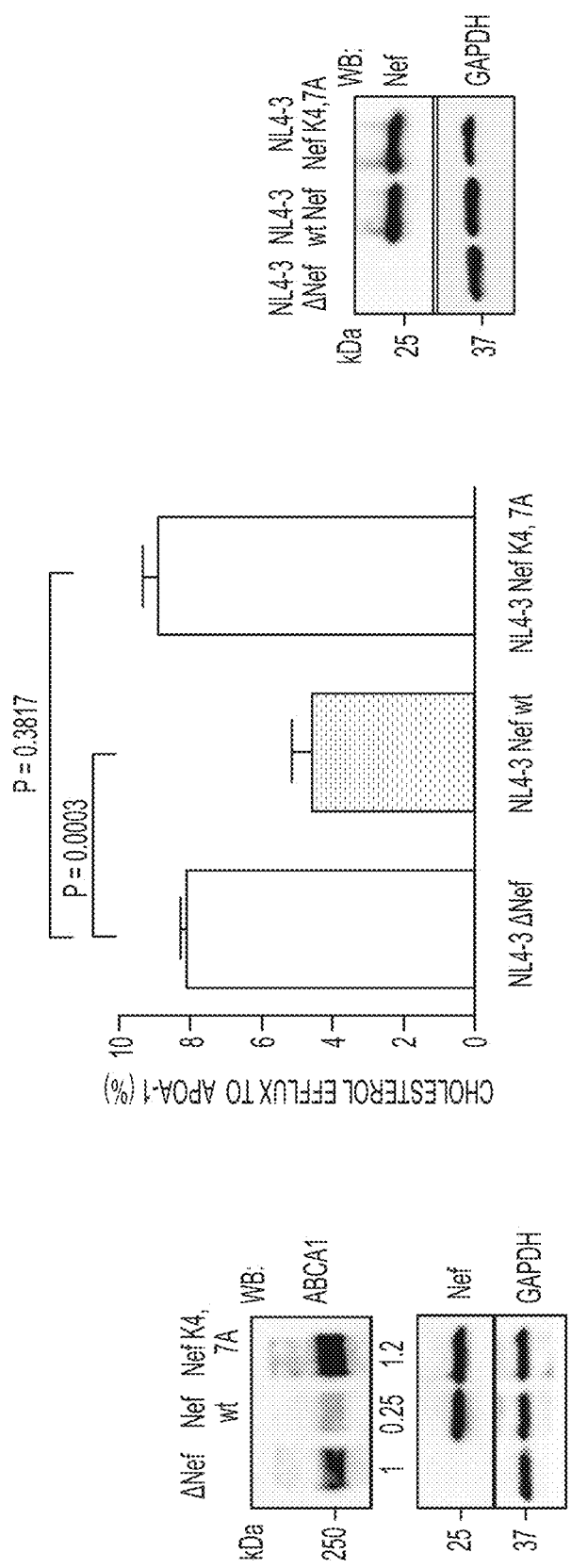
FIG. 4A shows the effects of the mutation of certain residues on Nef on regulation of ABCA1.
FIG. 4B shows the effects of the mutation of certain residues on Nef on cholesterol efflux.

In a previous study, it was reported that Nef plays a central role in the down-modulation of ABCA1 expression and function (1). This phenotype was associated with Nef's ability to interact with calnexin and disrupt calnexin interaction with ABCA1 (5). Identification of Nef residues required for interaction with calnexin provided an opportunity to verify the critical role of this interaction for the effects of Nef on cellular cholesterol metabolism. To assess the functional consequence of losing the Nef/CNX interaction for ABCA1 functionality, HEK293T cells were co-transfected with ABCA1 and HIV-1 NL4-3 infectious clones that express either Nef WT or Nef K4,7A. Lysates were immunoblotted for ABCA1 (FIG. 4A). Consistent with results obtained with Nef-expressing vector (FIG. 3C), total ABCA1 abundance was significantly reduced in the presence of Nef WT, however, expression of ABCA1 in the presence of Nef K4,7A was comparable to that of the control sample, which was transfected with an empty vector. This result is consistent with conclusions of the previous study that identified Nef as the key viral factor responsible for ABCA1 downregulation (1).

FIG. 3 shows various immunoprecipitation results displaying the interaction between Nef and Calnexin as a result of various conditions. Specifically, Panel A shows HEK293T cells transfected with HIV-1 molecular clones encoding for Nef WT or Nef K4,7A. Panel B shows HEK293T cells transfected with pcDNA plasmids expressing Nef WT or mutants Nef K4A, Nef K7A or NefK4,7A. Cells were lysed 48 h post-transfection. Endogenous calnexin was immunoprecipitated using monoclonal calnexin antibody and immunoprecipitates were blotted for Nef and calnexin (top panels). Whole cell lysates were analyzed for expression of calnexin (CNX), Nef and GAPDH (bottom panels). In panel (C), HEK293T cells were co-transfected with ABCA1-FLAG and Nef WT or mutants Nef K4A, Nef K7A or Nef K4,7A. Cells were lysed 48 h post-transfection and lysates were analyzed for expression of ABCA1, Nef and GAPDH. In panel (D) HEK293T cells were co-transfected with ABCA1-FLAG and Nef WT or NefK4,7A and were lysed 48 h post-transfection. ABCA1 was immunoprecipitated using anti-FLAG beads and precipitates were blotted for ABCA1 and Nef (top panel). Whole cell lysates were analyzed for expression of ABCA1-FLAG, Nef and GAPDH (bottom panel). Numbers under the lanes show relative amounts of co-precipitated Nef obtained by gel densitometry.

The effect of mutations disrupting Nef/CNX interaction on the ability of Nef to downregulate apoA-1 specific cholesterol efflux was evaluated. Monocyte derived macrophages were infected with HIV-1 expressing either wild-type Nef or Nef K4,7A. Given that the virus carrying the mutation was the X4-tropic strain NL4-3, it was pseudotyped with VSV-G to ensure one-cycle infection. Seven days after infection, cholesterol efflux assay was performed. In agreement with previous reports (1, 5, 28), cells infected with the wild-type virus had significantly reduced cholesterol efflux relative to mock-infected cells (FIG. 4B). However, infection with the virus carrying Nef K4,7A did not lead to efflux decrease.

FIG. 4 shows various assays showing the effects of the mutation of certain residues on Nef on regulation of ABCA1 and cholesterol efflux. Specifically, in panel (A) HEK 293T cells were co-transfected with ABCA1 and HIV-1 molecular clones encoding Nef WT or Nef K4,7A (HIV-1 clone with a Nef deletion was used as control). Cells were lysed 48 h post-transfection and immunoblotted for ABCA1, Nef and GAPDH. In panel (B), THP-1 cells were infected with HIV-1 molecular clones pseudotyped with VSV-G consisting of a Nef deletion (ΔNef) or expressing Nef WT or mutant Nef K4,7A. Cholesterol efflux was measured 13 days after infection. Results show apoA-I specific cholesterol efflux as mean±SEM of quadruplicates. Western blot shows expression of Nef in cell lysates.

Interaction Between Nef and Calnexin is Direct

Figure 5A:
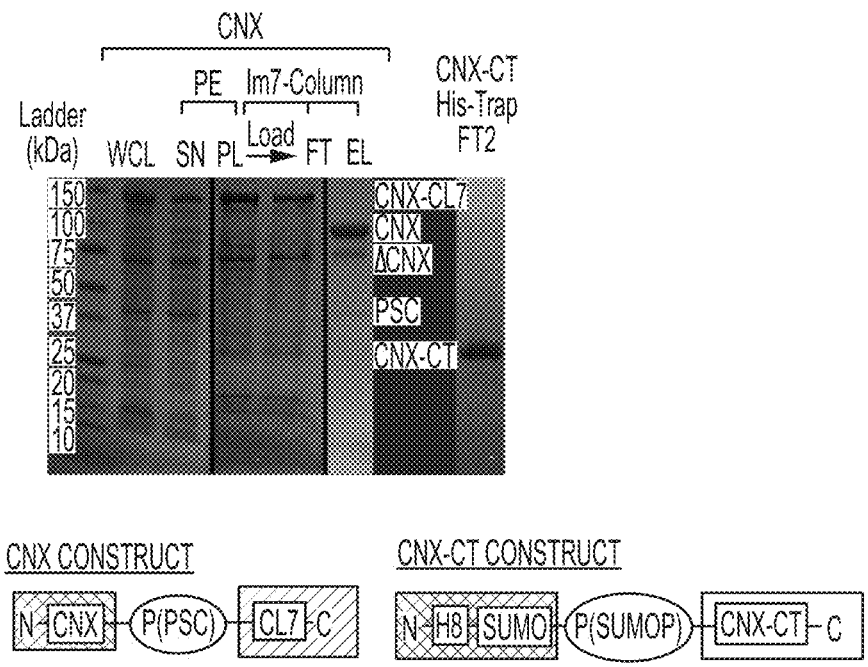
FIG. 5A shows the results of immunoprecipitation assays showing that Nef directly binds to Calnexin and its cytoplasmic tail.

To test whether Nef and calnexin interact directly with each other, CNX and the cytoplasmic tail of CNX (CNX-CT) was expressed in *E. coli* and purified recombinant proteins by column chromatography. For purification of full-length calnexin, a novel purification system based on the ultra-high affinity ($K_d\sim10^{-14}$-$10^{-17}$M) small protein complex of genetically inactivated colicin 7 DNAse (CL7) and its inhibitor, immunity protein 7 (Im7) (29-32) was developed and implemented. A CL7 variant, which possesses no DNAse activity but retains full Im7 affinity, was attached as a C-terminal tag on His-tagged calnexin construct (FIG. 5A, left side). A cleavage site for the pre-scission protease (PSC) inserted between CNX and CL7 allowed for elution of CNX from the Im7 column through cleavage by PSC. A single purification step provided an excellent yield of ~90% pure protein (FIG. 5A), in which major contamination represented CNX molecules (confirmed by mass-spec), most likely, truncated from the N-terminus. The CNX-CT construct was designed with a single N-terminal His-tag and was purified using the standard procedure (FIG. 5A, right side).

Figure 5B:
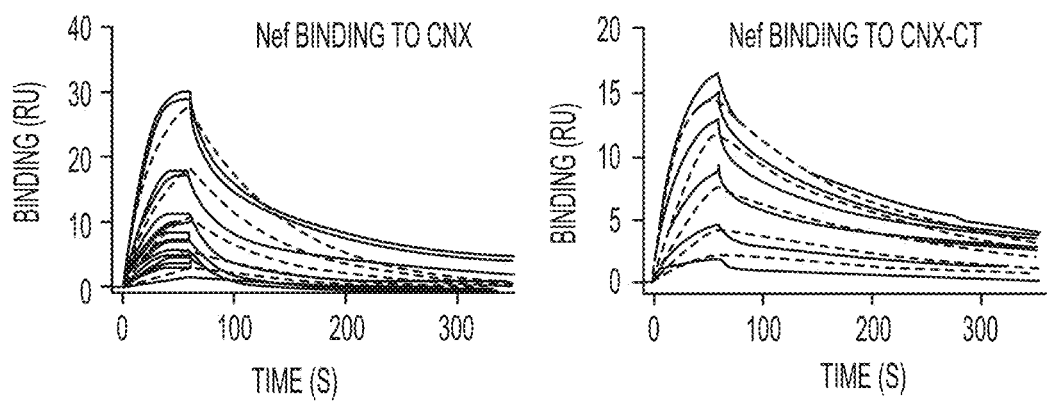
FIG. 5B is a graph mapping Nef binding to Calnexin and its cytoplasmic tail.

Binding of myristoylated $Nef_{SF2}$ (33) to CNX and its cytoplasmic domain was analyzed using surface plasmon resonance (FIGS. 5B,C). CNX and CNX-CT were immobilized on microchip surfaces and myristoylated Nef was injected over the surface. $Nef_{SF2}$ directly bound to calnexin with an affinity ($K_D$) of 89.1 nM ($k_a$=1.338E5 $M^{-1}s^{-1}$, $k_d$=0.01192 $s^{-1}$, $Chi^2$=2.77 RU) (FIG. 5B). Binding to CNX-CT was observed to have higher affinity of $K_D$=9.4 nM ($k_a$=9.083E5 $M^{-1}$ $s^{-1}$, $k_d$=0.008569 $s^{-1}$, $Chi^2$=0.474 RU) (FIG. 5C). Taken together, these experiments demonstrate that Nef/CNX interaction is direct and involves the cytoplasmic domain of calnexin.

FIG. 5 shows the results of immunoprecipitation assays showing that Nef directly binds to Calnexin and its cytoplasmic tail. Specifically, panel (A) shows purification of CNX and CNX-CT. Steps of full-length CL7-tagged calnexin (CNX-CL7) purification are shown in detail. Whole cell lysate (WCL) was centrifuged to remove cell debris, the supernatant (SN) was treated with 0.07% polyethyleneemine (PE) to precipitate DNA, the pellet (PL), which contained most of CNX protein, was washed with detergent-containing buffer to release CNX into solution, centrifuged and the resulting supernatant was loaded on Immunity protein 7 (Im7) column. Bound proteins were eluted by treating the column with pre-scission protease (PSC) (EL lane), whereas flow-through (FT) lane shows unbound proteins. Δ—CNX truncated CNX fragment; SUMO—SUMO domain; P(PSC), P(SUMOP)—cleavage sites for the PSC and SUMO proteases, respectively; H8—8-Histidine tag (SEQ ID NO: 2). In panels (B) and (C), surface plasmon resonance experiments were done in a Biacore T-200 by using a CM5 chip. Panel (B) shows CNX and Panel (C) shows CNX-CT proteins captured by amine coupling and myristoylated NefSF2 protein injected over the chip surface at 6 different concentrations (6.25 nM-200 nM range) in triplicates. Lines representing actual data and a curve fit to a monovalent analyte binding model in BiaEvaluation software are shown.

Virtual Screening for Compounds Interfering with Nef/CNX Interaction

Docking-based virtual screening has been performed on compounds from the Zinc NCI Plated 2007 dataset with docking program Vina (34). Nef model described in FIG. 2 has been used, with the interaction site for ligand docking selected to cover amino acid residues Lys4 and Lys7. The dataset consisted of 139,735 compounds. Ten putative ligands were identified and prioritized according to the Vina ranking, and structural alignment of these compounds to the Nef-CNX complex is shown in FIG. 6A (panel a). The model shows that these compounds can block Nef/CNX interaction at the CNX residues Glu529, Glu532 and Glu533. Docking of NSC 13987, which turned out in the later studies to be the most effective inhibitor of the Nef-CNX interaction, is shown in panel b (FIG. 6A). Interactions of the compound with Nef include two hydrogen bonds with Nef amino acid residues Ser6 and Tyr124. Three of the 10 compounds, NSC 1758, NSC 13987, and NSC 92938 have been submitted for experimental testing. The chemical names and molecular structures of these compounds are shown in FIG. 6B.

Testing the Compounds' Activity

To test whether the compounds identified in the virtual screen can interfere with Nef/CNX interaction, a co-immunoprecipitation assay was performed. HEK293T cells were transfected with plasmid encoding for Nef$_{BRU}$ and 6 h post-transfection were treated with NSC 1758 (4 µM), NSC 13987 (5 µM), or NSC 92938 (5 µM). These concentrations of the compounds were determined by the MTT assay to reduce cell metabolism by less than 10% during 5-day incubation (FIG. 6C). Among the 3 compounds tested, one compound, NSC 13987, inhibited co-immunoprecipitation of Nef and calnexin by over 50%, whereas the effect of NSC 1758 and NSC 92938 showed a trend towards inhibiting Nef/CNX binding but did not reach statistical significance (FIG. 6D). It was previously shown that membrane localization of Nef is important for interaction of Nef with calnexin (5). In order to rule out the possibility that the compound interferes with membrane localization of Nef, it was tested whether NSC 13987 affects interaction between Nef and ABCA1, as ABCA1/Nef interaction also requires membrane localization of Nef (1). As shown in FIG. 6E, ABCA1/Nef interaction remained unaffected in the presence of compound indicating that the inhibition was specific to the molecular interaction of Nef and CNX.

FIG. 6 shows the structures of various small molecules targeting the Nef-Calnexin interaction as well as the effects these molecules have on the Nef-Calnexin. Specifically, panel (A) a, shows the results of ten compounds with the best score (grey) from virtual screening performed on the Zinc NCI Plated 2007 dataset. Their overall location in the structural alignment with the model of Nef—CNX complex is shown as translucent molecular surface. The model shows that these compounds can block the Nef/CNX interaction at calnexin residues Glu529, Glu532 and Glu533. The set of compounds includes NSC 1758, NSC 13987, and NSC 92938 selected for experimental testing. b, Compound NSC 13987 docked to Nef binding site, which is centered on Lys4 and Lys7. Interactions of the compound with Nef include two hydrogen bonds with Nef amino acid residues Ser6 and Tyr124. Panel (B) shows the chemical structure and name of compounds NSC 1758, NSC 13987, and NSC 92938. Panel (C) shows the dose-response effect of NSC 1758, NSC 13987 and NSC 92938 on viability of THP-1 cells. THP-1 cells were treated with indicated compounds for 5 days and cytotoxicity was measured using MTT assay. In panel (D), HEK 293T cells were transfected with HA-tagged Nef, treated with compounds NSC 1758, NSC 13987 or NSC 92938, and lysed. Nef was immunoprecipitated using anti-HA agarose beads and bound complexes were immunoblotted for Nef and calnexin (left panels labeled IP: αHA). Densitometric quantification of calnexin co-immunoprecipitation with Nef is presented in the right panel. Error bars indicate +/−SD of 3 independent experiments, and p values are shown above the bars. Whole cell lysates were analyzed for amount of calnexin, Nef and GAPDH (left panels labeled Lysate). In panel (E), HEK293T cells were co-transfected with ABCA1-FLAG and Nef$_{BRU}$ and treated with compound NSC 13987. Cells were lysed 48 h post-transfection and ABCA1-FLAG was immunoprecipitated using anti-FLAG beads. Precipitated complexes were blotted for ABCA1 and Nef (top panels). Input amount was analyzed from whole cell lysates by immunoblotting for ABCA1, Nef and GAPDH (bottom panels).

Next, it was tested whether the three compounds could prevent impairment of cholesterol efflux by Nef. THP-1 cells were transfected with a Nef encoding plasmid and drug treatment was started 6 h after transfection. The following day cells were activated with PMA after which cholesterol efflux assay was performed. Drug treatment was continued throughout the duration of the experiment. FIG. 7A shows cholesterol efflux measured in untreated cells or cells treated with DMSO or each of the 3 compounds. Cholesterol efflux in Nef-transfected untreated or DMSO-treated cells was reduced by over 2-fold relative to mock-transfected cells. NSC 13987, which showed inhibition of Nef/CNX interaction (FIG. 6D), significantly increased cholesterol efflux as compared to DMSO-treated Nef expressing cells, although the rescue was not complete. Two other compounds did not significantly rescue Nef-suppressed cholesterol efflux.

To test the effect of NSC 13987 in the context of natural infection, monocyte-derived macrophages (MDM) were infected with HIV-1 ADA, treated with NSC 13987 and cholesterol efflux was measured. Viral replication in the presence of the compound was reduced (FIG. 7B), consistent with demonstrated rescue by the compound of Nef-inhibited cholesterol efflux (FIG. 7A) and previous studies demonstrating anti-HIV activity of ABCA1 and ABCA1-stimulated cholesterol efflux (28, 35, 36). Consistent with previous studies (1, 5, 36), cholesterol efflux from HIV-infected cells was decreased by 60%, whereas HIV-infected cells treated with NSC 13987 showed cholesterol efflux not significantly different from that of mock-infected cells (FIG. 7C). Taken together, these results provide a proof of concept for the idea that HIV-induced impairment of cholesterol efflux can be reversed pharmacologically by blocking the Nef/CNX interaction.

FIG. 7 shows graphs showing that an embodiment of the invention, compound NSC 13987, prevents impairment of cholesterol efflux by HIV and Nef. Specifically, in panel (A) THP-1 cells were transfected with Nef and incubated with compounds NSC 1758, NSC 13987 and NSC 92938 or DMSO, and cholesterol efflux was measured 5 days post-transfection. Error bars show SEM. In panel (B) primary macrophages were infected in triplicate with HIV-1 ADA. Compound NSC 13987 (5 µM) or DMSO was added 3 days after infection and maintained thereafter, and virus replication was monitored by measuring RT-activity in the supernatant over a 14-day period. Results of 3 measurements are shown as mean±SEM. *, $p<0.005$; **, $p<0.007$. In panel (C) primary macrophages were infected with HIV-1 ADA or mock-infected and treated with DMSO or NSC13987 as in panel B. Cholesterol efflux was measured 14 days post-infection. Error bars show SEM.

Discussion

In this example, a small-molecule compound that blocks HIV-mediated impairment of cellular cholesterol metabolism was identified. Excitingly, this compound also inhibited replication of HIV, suggesting that, if developed into a drug, it can target both HIV infection and virus-induced metabolic co-morbidities.

Previous studies demonstrated that HIV critically depends on interaction with host cholesterol metabolism and modifies it for optimization of viral replication (1, 2, 28, 35, 36). Specifically, HIV, through viral protein Nef, reduces abundance and impairs functional activity of ABCA1, a key transporter in cholesterol efflux pathway (1). As a result, host cells accumulate excessive cholesterol promoting formation of plasma membrane lipid rafts, which are sites of HIV entry, assembly and budding (39). Recently, it was demonstrated that an important mechanism of down-regulation and/or functional impairment of ABCA1 by HIV is Nef-mediated inhibition of the interaction between ABCA1 and the ER chaperone, calnexin (5). The current study provides the first characterization of the exact molecular structures involved in Nef-CNX interaction.

First, it was established that interaction between Nef and calnexin involves the cytoplasmic domain of calnexin. While this finding is consistent with demonstrated localization of Nef to the cytoplasmic side of membranes (27) and lack of evidence for Nef localization to ER, it is surprising given that the C-tail of calnexin is not involved in the interaction between calnexin and ABCA1, which is disrupted by Nef (5). Indeed, calnexin interactions with glycosylated proteins are mediated by its lumenal domains (12). Therefore, Nef interaction with the C-tail alters activity of the lumenal domains of calnexin. How Nef is doing it is unknown and several possibilities can be considered. Binding of Nef may prevent post-translational modifications of the C-tail of calnexin, such as phosphorylation on Ser563 that has been shown to regulate calnexin interaction with al-antitrypsin and a number of other glycoproteins (15). However, docking analysis did not reveal Ser563 as a likely site for interaction with Nef (FIG. 5B). The same argument can be applied to SUMOylation at Lys506, which has been shown to regulate calnexin interaction with another ER protein, protein tyrosine phosphatase 1B (40): Lys506 is not among the preferred sites for Nef binding. It is possible that Nef binding itself induces a conformational change in calnexin extending to its lumenal domains, but mechanistic details of such an effect await careful structural analysis. Regardless of the mechanism, this finding provides the first example of a pathogen utilizing the calnexin C-tail to regulate functional activity of this chaperone.

Second, the Nef residues critical for interaction with calnexin were identified: mutation of lysine residues in positions 4 and 7 of Nef abrogated Nef/CNX binding, prevented ABCA1 downregulation, and restored cholesterol efflux in cells infected with HIV-1. The finding that Nef/CNX interaction involves the flexible N-terminal region of Nef was surprising, as this region has not been implicated before in protein-protein interactions. However, molecular modeling (FIG. 2) suggests that Lys4 of Nef forms a hydrogen bond with Asp90 located in an alpha-helix, thus contributing to stabilization of the structure of the N-terminal region, and therefore acts as a structural anchor for the Nef Lys7 interaction with calnexin. Nef Lys7 is predicted to form a strong interaction with Glu533 in calnexin through the hydrogen and ionic bonds. Thus, mutation of both lysine residues destabilizes the structure of Nef, and cancels the strong interaction with calnexin provided by Lys7, which explains the dramatic effect of these mutations on Nef/CNX interaction. The N-terminal region of Nef has not been involved in protein-protein interactions, but its basic and hydrophobic residues were shown to be essential for membrane association of Nef (41). Interestingly, lysine residues at positions 4 and 7, which participate in interaction with calnexin, were not essential for the membrane association of Nef (42). Therefore, this study a novel epitope on Nef involved in the interaction with the cytoplasmic tail of calnexin was identified.

Using this information, a virtual screening for compounds that can potentially disrupt Nef-CNX interaction was performed, and a number of candidates were identified. One of these compounds, 1[(7-Oxo-7H-benz[de]anthracene-3-yl) amino]anthraquinone (NSC 13987), prevented co-precipitation of CNX with Nef, reversed Nef-mediated effect on ABCA1 abundance, and restored cholesterol efflux impaired by Nef, thus effectively reversing the effects of Nef on host cholesterol metabolism. In addition, the compound resulted in a near 2-fold inhibition of viral replication (FIG. 7B). This latter effect may have two main explanations. First, the compound prevents ABCA1 downregulation by Nef, and ABCA1 has been shown to inhibit HIV-1 replication by reducing lipid rafts abundance on the plasma membrane and affecting production and infectivity of nascent virions (3, 28, 35, 36). Second, previous reports presented evidence that anthraquinone derivatives inhibit the ribonuclease H function of HIV-1 reverse transcriptase (43, 44). These findings provide basis for using NSC 13987 as a foundation for development of novel treatment approaches based on targeting the interaction of HIV with host cholesterol metabolism. Based on the known effects of OCR agonists, it is unlikely that this approach would generate a stand-alone treatment for HIV. However, it may effectively supplement current treatment regimens significantly increasing their efficiency and/or allowing for reduction of doses. Furthermore, the effects of Nef secreted from HIV-infected cells may be responsible for many lipid-related complications of HIV disease, such as atherosclerosis, diabetes, lipodistrophy and neurodegeneration. The approach proposed in this study will also reverse HIV-induced impairment of cholesterol metabolism in uninfected cells mitigating lipid-related complications of HIV infection in addition to contributing to the treatment of HIV itself.

Calnexin is an ER-integral membrane protein and is responsible for the folding of several glycoproteins. Depletion of calnexin has been shown to result in the elevation of several other ER-folding factors minimizing aberrant protein folding and expression (45). This is mainly true for glycoproteins which are common substrates of other soluble ER chaperones like calreticulin. However, solubility and oligosaccharide variability impose a limit on this commonality making calnexin vital for expression and function of proteins like ABCA1 and several others (5, 46, 47). Nef's ability to target several host factors, such as CD4, MHC I, CXCR4, may in part be due to the limitation it imposes on their access to chaperone proteins like calnexin. Therefore, the positive effect of compound NSC13987 may well extend to restoring the expression and function of other proteins targeted by Nef.

In conclusion, in this study the molecular mechanisms and exact structures involved in interaction between HIV Nef and host canexin were identified and a compound capable of reversing the effects of Nef was characterized, thus presenting potential utility in treatment of HIV infection and its metabolic side effects.

Experimental Procedures

Reagents—The following reagents were purchased from the indicated suppliers: mouse monoclonal anti-calnexin (ab31290, Abcam); anti-HA Epitope tag Antibody (NB600-363, Novus Biologicals); anti-Nef serum (NIH AIDS Reagent Program); anti-ABCA1 (NB400-105, Novus Biologicals); polyclonal rabbit anti-calnexin (H-70, Santa Cruz Biotech); anti-GAPDH (G9545, Sigma Aldrich); HRP conjugated donkey anti-rabbit and Goat anti-mouse (Jackson Immuno Research); anti-HA Agarose (26181, Thermo Scientific); EZview Red Protein A Affinity Gel (P6486, Sigma- Aldrich). Metafectene® (Biontex; IGEPAL (CA-630, SigmaAldrich); Triton™ (X-100, Sigma Aldrich); 10% SDS (Corning).

Nef and Calnexin Mutagenesis—Nef expression plasmid pcDNA3.1 Nef was obtained through the NIH AIDS Reagent Program (Cat #11431) from Dr. J. Victor Garcia. The Nef insert was cloned by PCR using primers as previously described (48) and was mutagenized. Nef mutants K4A, K7A and K4,7A were generated from the pcDNA3.1 NefBRU plasmid using site-directed mutagenesis with Pfu Ultra High-Fidelity DNA Polymerase (Agilent Technologies). Forward and reverse primer sequences used were as follows: Nef K4A Fwd, 5'-TTTGCTATAAGATGGGTGGCGCGTGGTCAAAAAGTAGTGTGG-3' (SEQ ID NO: 3), Rev 5'-CCACACTACTTTTTGAC-CACGCGCCACCCATCTTATAGCAAA-3' (SEQ ID NO: 4); Nef K7A Fwd, 5'GATGGGTGGCAAGTGGTCAGCAAGTAGTGTGGTTG-GATGG-3' (SEQ ID NO: 5), Rev 5'-CCATCCAAC-CACACTACTTGCTGACCACTTGCCACCCATC-3 (SEQ ID NO: 6) and NefK4,7A FWD 5'-GGGTGGCGCGTGGTCAGCAAGTAGTGTGGTTGGA-3' (SEQ ID NO: 7), Rev 5'-TCCAACCACAC-TACTTGCTGACCACGCGCCACCC-3' (SEQ ID NO: 8). Resulting cDNA was transformed into XL10-Gold Ultracompetent Cells and final plasmid preps were sequenced to confirm mutations. The plasmid pCG-NL4-3-IRES-GFP was kindly provided by the lab of Dr. Marc Harris (27).

Human CNX cDNA construct with a C-terminal HA tag was prepared by standard PCR method from CNX cDNA clone (Open Biosystems) in the pHCMV3 vector (Gelantis). Truncated CNX construct was generated similarly by using primers described previously (49). The HA-tagged $CNX_{\Delta504-586}$ construct lacks the 87 residues of the cytoplasmic tail. Deletion of the repeated sequence motifs referred to as $CNX_{\Delta276-409}$ was made by restriction digest of full length HA-tagged pHCMV3-CNX and re-ligation (46).

Expression and Purification of Calnexin—

A CNX expression vector with a His-tag at the N-terminus and the CL7-tag was designed, which can be cleaved by the PSC protease, at the CNX C-terminus (FIG. 5A). The CNX-CT construct was designed with a single N-terminal His-tag followed by the SUMO-domain (to allow His-tag cleavage by the SUMO-protease, SUMO-P). CNX and CNX-CT were expressed in E. coli BL21 DE. Cells were grown at 37° C. to OD~0.8-0.9, then temperature was decreased to 18-20° C. and expression was induced with 0.1 mM IPTG overnight. Cells were frozen at −80° C. until protein purification.

A novel purification system based on the natural ultra-high affinity complex ($K_m$~$10^{-14}$-$10^{-17}$ M) between the colicin E7 DNAse domain (CL7) and its inhibitor, immunity protein 7 (Im7) (29-32) was developed and implemented. The proteins have been modified to remove DNAse activity of CL7 and allow for efficient immobilization of the Im7 unit on the activated agarose beads (DGV, unpublished results). The CNX construct tagged at the C-terminus with CL7 was expressed in E. coli, the cells were lysed, centrifuged to remove cell debris, and the supernatant was treated with 0.07% polyethylene-emine (PE) to precipitate CNX (FIG. 5A). The pellet was washed with 20 mM Tris-HCl, pH 8.0, 600 mM NaCl, 1.5% dodecyl-maltopyranoside to release CNX into solution, centrifuged again, and the resulting supernatant was loaded on the Im7 column. CNX protein was eluted from the column upon treatment by PSC protease. This single purification step provided an excellent yield of ~90-95% pure protein, in which major contamination represents truncated CNX molecules (confirmed by mass-spectroscopy). Given that these molecules are retained on the column and that affinity tag is localized at the C-terminus of CNX, truncation occurred most likely from the N-terminus (proteolytic sensitivity of CNX at the N-end was reported previously (50)). CNX-CT was purified in standard procedure using the commercial His-Trap column. All procedures were carried out at 4° C.

Surface Plasmon Resonance Experiments—

Direct binding between purified recombinant proteins was evaluated by surface plasmon resonance technology utilizing a Biacore T-200 instrument at the Biacore Molecular Interaction Shared Resource of Georgetown University. Full length CNX and the C-terminal (cytoplasmic) domain of CNX (CNX-CT) were captured on CM5 chips by amine coupling. Three surfaces of CM5 chip were activated by NHS/CDC (N-hydroxysuccinimide/1-ethyl-3-(3-dimethyl-aminopropyl)carbodiimide hydrochloride) for 720 sec. Flow cell 1 was left empty as a reference surface. Full length CNX and CNX-CT were diluted in 10 mM sodium acetate (pH 4.0) buffer at 1.8 µM and 10.6 µM, respectively, and captured on flow cell 3 and flow cell 2, at 3200 RU and 16600 RU, respectively. After protein capture, all 3 flow cells were inactivated by 720 sec injection of 1 M ethanolamine. Myristoylated $Nef_{SF2}$ protein was injected over the chip surface at 6 different concentrations (6.25 nM, 12.5 nM, 25 nM, 50 nM, 100 nM, 200 nM) in triplicates. All binding studies were done at 25° C. Flow rate for protein capture was 10 µl/min, and kinetics experiment was at 50 µl/min. HPS-P (10 mM HEPES pH 7.4, 150 mM NaCl, 0.005% surfactant P-20)+2 mM $CaCl_2$ was used as the running buffer. The data was analyzed by BiaEvaluation software using the bivalent analyte model.

Cells and Transfection—

HEK293T and THP-1 cells were cultured in RPMI supplemented with 10% fetal bovine serum and antibiotics. For transfection, 293T cells were passaged and cultured overnight in 6-well plates and transfected with plasmid DNA using Metafectene according to the manufacturer's (Biontex) instructions.

Compounds—

Three out of 10 compounds obtained from NCI drug database were tested for blocking Nef/CNX interaction. Tested compounds were 1,3-DI-9-Phenanthrylguanidine (NSC 1758), 1[(7-Oxo-7H-benz[de]anthracene-3-yl)amino]anthraquinone (NSC 13987) and 5H-Naphtho(2,3-a)carbazole-5,13(12H)-dione (NSC 92938). All compounds were dissolved in DMSO and diluted in cell culture medium (RPMI 1640 with 10% fetal bovine serum and antibiotics) to ensure the final concentration of the solvent to be <1%.

MTT Assay—

THP-1 cells were seeded in 96 well plates (30,000 cells/well) and incubated at 37° C., 5% $CO_2$ in the presence of compounds for 5 days. The MTT assay for cytotoxicity was done in quadruplicates according to manufacturer's instructions (Sigma-Aldrich). The concentrations selected for experimental testing—4 µM for NSC 1758, and 5 µM for NSC 13987 and NSC 92938—reduced MTT metabolism by less than 10% relative to untreated cultures.

Immunoprecipitation—

For calnexin mutant/Nef interaction analysis, HEK293T cells were transfected with HA-tagged calnexin mutants and $Nef_{BRU}$ expression plasmid. Cells were lysed 48 h post-transfection with 1% IGEPAL and 0.1% SDS lysis buffer on ice for 30 min. Lysates were incubated with anti-HA agarose beads for 2 h at 4° C. with rotation. Respective immunoprecipitates were washed three times with TBS (150 mM NaCl, 30 mM Tris-HCl, 5 mM EDTA, pH 7.5). Bound complexes were eluted by boiling in sample buffer for 5 min. Supernatants were separated by SDS-PAGE for immunoblotting. Immunoprecipitation of calnexin from cells transfected with pCG-NL4-3-IRES-GFP or mutant variant was performed similarly with the following modifications. Cell lysates were incubated with monoclonal anti-calnexin antibody for 2 h with rotation at 4° C. EZView protein A agarose beads were then added and the mix was further incubated for 1 h at 4° C. with rotation. Bound complexes were recovered as described above. For studies of Nef/CNX interactions in the presence of compounds, HEK293T cells were first transfected with HA-tagged Nef and compounds were added after 6 h. Cells were lysed 48 h post-transfection and immunoprecipitation was carried out using anti-HA agarose beads as described above.

Molecular Modeling and Docking—

Structure modeling of the calnexin cytoplasmic domain was performed using servers Hhpred (51), iTasser (52), ModWeb (53), Phyre2 (54), and RaptorX (55), with subsequent quality assessment of the obtained models and building of the final model by the QA-Recombinelt server (56). The Modbase (53) GI 66933005 model based on PDB 1JHN (96% sequence identity) was used for the lumenal domain structure. Nef structure has been modeled using as templates the crystallographic and solution NMR experimental structures covering different parts of Nef sequence, available from the PDB (57): 4EN2, 3TB8, 4EMZ, 3REB, 3RBB, 3REA, 1EFN. These structures are based on the HIV-1 sequences P03404, P03406, P03407, Q90VU7 (Uniprot (58)). Modeling was performed for the target sequence P03407 (HIV-1 group M subtype B isolate ARV2/BRU) with servers Hhpred, iTasser, M4T (59), ModWeb, Phyre2, Swiss-Model (60). The resulting models have been then submitted to the QA-Recombinelt server, producing the final model used for interactions prediction.

In order to obtain indications as to which regions of Nef can represent interactions interfaces, location of possible interactions sites has been estimated with a sequence-based method ConSurf (25). Sequence conservation for Nef has been assessed by constructing multiple alignments using T-Coffee (61). We have subsequently carried out docking of the structure models of calnexin cytoplasmic domain and Nef to identify the sites in Nef interacting with calnexin. Docking was performed using servers Cluspro (62), HEX (63), SwarmDock (64), Zdock (65), each run producing 10 best models. To obtain a representative array of docking models, docking has been carried out for calnexin and Nef submitted to docking runs alternatively as receptor and ligand. Since both calnexin cytoplasmic domain and Nef bind to ER membrane, the resulting docking models that were able to disrupt this binding have been filtered out from the final data.

To assess average number of interactions for each residue position in Nef and CNX sequences in the set of docking models of binding between CNX cytoplasmic domain and Nef, the overall number of Nef-CNX interactions for all models, for each residue in Nef and CNX involved in intermolecular interaction has been calculated. Number of interactions for each amino acid residue in Nef and CNX is the total number of interactions for this residue in docking models where such interaction was identified.

Virtual Screening— structure-based virtual screening (docking-based) was carried out on the NCI Plated 2007 dataset (http://zinc.docking.org/catalogs/ncip) from Zinc database (http://zinc.docking.org/)(66). Locally installed docking program AutoDock Vina (34) has been used for screening.

HIV Infection—

HIV particles pseudotyped with VSV-G were produced from HEK293T cells by transfecting with pCG-NL4-3-IRES-GFP or Nef mutant derivative. Monocyte-derived macrophages were infected with the respective wild-type or mutant virus particles normalized by RT activity. Infection was allowed to proceed for 10 days and the level of infection was monitored by RT assay.

Cholesterol Efflux—

Infected cells were seeded in a 24-well plate and labeled with [$^3$H] cholesterol for 48 h. Following this step, cells were washed with PBS to remove any free cholesterol and efflux was initiated by adding apoA-I (20 μg/mL) and incubating for 3 h in serum free medium. The media from the wells was then carefully collected and any cell debris was removed by centrifuging at 5,000 rpm for 5 min. Cell monolayers were lysed with 1% Triton X-100. Level of radioactivity in the media as well as in the cells was determined by scintillation counting. Cholesterol efflux was calculated as the percentage of radioactivity in the media divided by the total amount measured in the cells and media. Cholesterol efflux in the presence of compounds was performed similarly with the following modifications. THP-1 cells were first transfected with BRU Nef using Lipofectamine™ LTX reagent (ThermoFisher Scientific). Compounds were added to cells 6 h post transfection and incubated overnight. The following day cells were washed with PBS and treatment with compounds was continued for 48 h with the addition of [$^3$H] cholesterol and Phorbol 12-myristate 13-acetate (PMA). Efflux measurements were then performed as described above.

Nef Sequence(s)—

HIV-1 group M is the most is the most common type of HIV accounting for more than 90% of the AIDS epidemic. Within this group are several subtypes, the most common of which are Subtypes A-H. In the example above, a consensus Nef sequence (Nef consB).

The nucleotide sequence of this consensus sequence is:

```
                                              (SEQ ID NO: 9)
atgggtggcaagtggtcaaaacgtagtgtggttggatggcctgctgtaag ggaaagaatgagacgagctgagccagcagcagatgggtgggagcagtat ctcgagacctggaaaaacatggagcaatcacaagtagcaatacagcagct aacaatgctgattgtgcctggctagaagcacaagaggaggaggaggtggg ttttccagtcagacctcaggtacctttaagaccaatgacttacaaggcag ctgtagatcttagccacttttaaaagaaaagggggactggaagggcta atttactcccaaaaaagacaagatatccttgatctgtgggtctaccacac acaaggctacttccctgattggcagaactacacaccagggccagggatca gatatccactgacctttggatggtgcttcaagctagtaccagttgagcca gagaaggtagaagaggccaatgaaggagagaacaacagcttgttacaccc tatgagcctgcatgggatggatgacccggagaaagaagtgttagtgtgga agtttgacagccgcctagcatttcatcacatggcccgagagctgcatccg gagtactacaaggactgctga
```

The amino acid sequence of the consenus sequence is:

(SEQ ID NO: 10)
MGGKWSKRSVVGWPAVRERMRRAEPAADGVGAVSRDLEKHGAITSSNTAA

NNADCAWLEAQEEEEVGFPVRPQVPLRPMTYKAAVDLSHFLKEKGGLEGL

IYSQKRQDILDLWVYHTQGYFPDWQNYTPGPGIRYPLTFGWCFKLVPVEP

EKVEEANEGENNSLLHPMSLHGMDDPEKEVLVWKFDSRLAFHHMARELHP

EYYKDC.

This consensus sequence was previously developed by comparing the Nef sequences of the HIV Subtypes A-H (67). All Nef sequences of these HIV Subtypes have a conserved lysine at the 4<sup>th</sup> and 7<sup>th</sup> positions. The consensus sequence described in the example was specifically derived from HIV subtype B.

Calnexin sequence—

In the example above, the nucleotide sequence of Calnexin is:

(SEQ ID NO: 11)
ATGGAAGGGAAGTGGTTGCTGTGTATGTTACTGGTGCTTGGAACTGCTAT

TGTTGAGGCTCATGATGGACATGATGATGATGTGATTGATATTGAGGATG

ACCTTGACGATGTCATTGAAGAGGTAGAAGACTCAAAACCAGATACCACT

GCTCCTCCTTCATCTCCCAAGGTTACTTACAAAGCTCCAGTTCCAACAGG

GGAAGTATATTTTGCTGATTCTTTTGACAGAGGAACTCTGTCAGGGTGGA

TTTTATCCAAAGCCAAGAAAGACGATACCGATGATGAAATTGCCAAATAT

GATGGAAAGTGGGAGGTAGAGGAAATGAAGGAGTCAAAGCTTCCAGGTGA

TAAAGGACTTGTGTTGATGTCTCGGGCCAAGCATCATGCCATCTCTGCTA

AACTGAACAAGCCCTTCCTGTTTGACACCAAGCCTCTCATTGTTCAGTAT

GAGGTTAATTTCCAAATGGAATAGAATGTGGTGGTGCCTATGTGAAACT

GCTTTCTAAAACACCAGAACTCAACCTGGATCAGTTCCATGACAAGACCC

CTTATACGATTATGTTTGGTCCAGATAAATGTGGAGAGGACTATAAACTG

CACTTCATCTTCCGACACAAAAACCCCAAAACGGGTATCTATGAAGAAAA

ACATGCTAAGAGGCCAGATGCAGATCTGAAGACCTATTTTACTGATAAGA

AAACACATCTTTACACACTAATCTTGAATCCAGATAATAGTTTTGAAATA

CTGGTTGACCAATCTGTGGTGAATAGTGGAAATCTGCTCAATGACATGAC

TCCTCCTGTAAATCCTTCACGTGAAATTGAGGACCCAGAAGACCGGAAGC

CCGAGGATTGGGATGAAAGACCAAAAATCCCAGATCCAGAAGCTGTCAAG

CCAGATGACTGGGATGAAGATGCCCCTGCTAAGATTCCAGATGAAGAGGC

CACAAAACCCGAAGGCTGGTTAGATGATGAGCCTGAGTACGTACCTGATC

CAGACGCAGAGAAACCTGAGGATTGGGATGAAGACATGGATGGAGAATGG

GAGGCTCCTCAGATTGCCAACCCTAGATGTGAGTCAGCTCCTGGATGTGG

TGTCTGGCAGCGACCTGTGATTGACAACCCCAATTATAAAGGCAAATGGA

AGCCTCCTATGATTGACAATCCCAGTTACCAGGGAATCTGGAAACCCAGG

AAAATACCAAATCCAGATTTCTTTGAAGATCTGGAACCTTTCAGAATGAC

TCCTTTTAGTGCTATTGGTTTGGAGCTGTGGTCCATGACCTCTGACATTT

TTTTTGACAACTTTATCATTTGTGCTGATCGAAGAATAGTTGATGATTGG

GCCAATGATGGATGGGGCCTGAAGAAAGCTGCTGATGGGGCTGCTGAGCC

AGGCGTTGTGGGGCAGATGATCGAGGCAGCTGAAGAGCGCCCGTGGCTGT

GGGTAGTCTATATTCTAACTGTAGCCCTTCCTGTGTTCCTGGTTATCCTC

TTCTGCTGTTCTGGAAAGAAACAGACCAGTGGTATGGAGTATAAGAAAAC

TGATGCACCTCAACCGGATGTGAAGGAAGAGGAAGAAGAGAAGGAAGAGG

AAAAGGACAAGGGAGATGAGGAGGAGGAAGGAGAAGAGAAACTTGAAGAG

AAACAGAAAAGTGATGCTGAAGAAGATGGTGGCACTGTCAGTCAAGAGGA

GGAAGACAGAAAACCTAAAGCAGAGGAGGATGAAATTTTGAACAGATCAC

CAAGAAACAGAAAGCCACGAAGAGAGTGA

The amino acid sequence is:

(SEQ ID NO: 12)
MEGKWLLCMLLVLGTAIVEAHDGHDDDVIDIEDDLDDVIEEVEDSKPDTT

APPSSPKVTYKAPVPTGEVYFADSFDRGTLSGWILSKAKKDDTDDEIAKY

DGKWEVEEMKESKLPGDKGLVLMSRAKHHAISAKLNKPFLFDTKPLIVQY

EVNFQNGIECGGAYVKLLSKTPELNLDQFHDKTPYTIMFGPDKCGEDYKL

HFIFRHKNPKTGIYEEKHAKRPDADLKTYFTDKKTHLYTLILNPDNSFEI

LVDQSVVNSGNLLNDMTPPVNPSREIEDPEDRKPEDWDERPKIPDPEAVK

PDDWDEDAPAKIPDEEATKPEGWLDDEPEYVPDPDAEKPEDWDEDMDGEW

EAPQIANPRCESAPGCGVWQRPVIDNPNYKGKWKPPMIDNPSYQGIWKPR

KIPNPDFFEDLEPFRMTPFSAIGLELWSMTSDIFFDNFIICADRRIVDDW

ANDGWGLKKAADGAAEPGVVGQMIEAAEERPWLWVVYILTVALPVFLVIL

FCCSGKKQTSGMEYKKTDAPQPDVKEEEEEKEEEKDKGDEEEEGEEKLEE

KQKSDAEEDGGTVSQEEEDRKPKAEEDEILNRSPRNRKPRRE.

It should be understood that various alternatives to the embodiments of the invention described herein may be employed in practicing the invention. It is intended that the scope of the invention, methods and structures within the scope of the invention includes equivalents.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

1. Mujawar Z, Rose H, Morrow M P, Pushkarsky T, Dubrovsky L, Mukhamedova N, Fu Y, Dart A, Orenstein J M, Bobryshev Y V, Bukrinsky M, Sviridov D. 2006. Human immunodeficiency virus impairs reverse cholesterol transport from macrophages. PLoS Biol 4:e365.
2. Asztalos B F, Mujawar Z, Morrow M P, Grant A, Pushkarsky T, Wanke C, Shannon R, Geyer M, Kirchhoff F, Sviridov D, Fitzgerald M L, Bukrinsky M, Mansfield K G. 2010. Circulating Nef induces dyslipidemia in simian immunodeficiency virus-infected macaques by suppressing cholesterol efflux. J Infect Dis 202:614-623.
3. Dubrovsky L, Van Duyne R, Senina S, Guendel I, Pushkarsky T, Sviridov D, Kashanchi F, Bukrinsky M. 2012. Liver X receptor agonist inhibits HIV-1 replication and prevents HIV-induced reduction of plasma HDL in humanized mouse model of HIV infection. Biochem Biophys Res Commun 419:95-98.
4. Cui H L, Ditiatkovski M, Kesani R, Bobryshev Y V, Liu Y, Geyer M, Mukhamedova N, Bukrinsky M, Sviridov D. 2014. HIV protein Nef causes dyslipidemia and formation of foam cells in mouse models of atherosclerosis. FASEB J 28:2828-2839.
5. Jennelle L, Hunegnaw R, Dubrovsky L, Pushkarsky T, Fitzgerald M L, Sviridov D, Popratiloff A, Brichacek B, Bukrinsky M. 2014. HIV-1 protein Nef inhibits activity of ATP-binding cassette transporter A1 by targeting endoplasmic reticulum chaperone calnexin. J Biol Chem 289: 28870-28884.
6. Helenius A, Aebi M. 2004. Roles of N-linked glycans in the endoplasmic reticulum. Annu. Rev. Biochem. 73:1019-1049.
7. Tanaka A R, Ikeda Y, be-Dohmae S, Arakawa R, Sadanami K, Kidera A, Nakagawa S, Nagase T, Aoki R, Kioka N, Amachi T, Yokoyama S, Ueda K. 2001. Human ABCA1 contains a large amino-terminal extracellular domain homologous to an epitope of Sjogren's Syndrome. Biochem Biophys Res Commun 283:1019-1025.
8. Pind S, Riordan J R, Williams D B. 1994. Participation of the endoplasmic reticulum chaperone calnexin (p88, IP90) in the biogenesis of the cystic fibrosis transmembrane conductance regulator. J Biol Chem. 269:12784-12788.
9. Loo T W, Clarke D M. 1994. Prolonged association of temperature-sensitive mutants of human P-glycoprotein with calnexin during biogenesis. J Biol Chem 269:28683-28689.
10. Okuhira K, Fitzgerald M L, Sarracino D A, Manning J J, Bell S A, Goss J L, Freeman M W. 2005. Purification of ATP-binding cassette transporter A1 and associated binding proteins reveals the importance of beta1-syntrophin in cholesterol efflux. J Biol Chem 280:39653-39664.
11. Chevet E, Wong H N, Gerber D, Cochet C, Fazel A, Cameron P H, Gushue J N, Thomas D Y, Bergeron J J. 1999. Phosphorylation by CK2 and MAPK enhances calnexin association with ribosomes. EMBO J 18:3655-3666.
12. Schrag J D, Bergeron J J, Li Y, Borisova S, Hahn M, Thomas D Y, Cygler M. 2001. The Structure of calnexin, an E R chaperone involved in quality control of protein folding. Mol Cell 8:633-644.
13. Roderick H L, Lechleiter J D, Camacho P. 2000. Cytosolic phosphorylation of calnexin controls intracellular Ca(2+) oscillations via an interaction with SERCA2b. J Cell Biol 149:1235-1248.
14. Myhill N, Lynes E M, Nanji J A, Blagoveshchenskaya A D, Fei H, Carmine S K, Cooper T J, Thomas G, Simmen T. 2008. The subcellular distribution of calnexin is mediated by PACS-2. Mol Biol Cell 19:2777-2788.
15. Cameron P H, Chevet E, Pluquet O, Thomas D Y, Bergeron J J. 2009. Calnexin phosphorylation attenuates the release of partially misfolded alpha1-antitrypsin to the secretory pathway. J Biol Chem 284:34570-34579.
16. Lynes E M, Bui M, Yap M C, Benson M D, Schneider B, Ellgaard L, Berthiaume L G, Simmen T. 2012. Palmitoylated TMX and calnexin target to the mitochondria-associated membrane. EMBO J 31:457-470.
17. Lynes E M, Raturi A, Shenkman M, Ortiz Sandoval C, Yap M C, Wu J, Janowicz A, Myhill N, Benson M D, Campbell R E, Berthiaume L G, Lederkremer G Z, Simmen T. 2013. Palmitoylation is the switch that assigns calnexin to quality control or E R Ca2+ signaling. J Cell Sci 126: 3893-3903.
18. Lakkaraju A K, Abrami L, Lemmin T, Blaskovic S, Kunz B, Kihara A, Dal Peraro M, van der Goot F G. 2012. Palmitoylated calnexin is a key component of the ribosome-translocon complex. EMBO J 31:1823-1835.
19. Ranki A, Lagerstedt A, Ovod V, Aavik E, Krohn K J. 1994. Expression kinetics and subcellular localization of HIV-1 regulatory proteins Nef, Tat and Rev in acutely and chronically infected lymphoid cell lines. Arch Virol 139: 365-378.
20. Grzesiek S, Bax A, Hu J S, Kaufman J, Palmer I, Stahl S J, Tjandra N, Wingfield P T. 1997. Refined solution structure and backbone dynamics of HIV-1 Nef. Protein Sci 6:1248-1263.
21. Akgun B, Satija S, Nanda H, Pirrone G F, Shi X, Engen J R, Kent M S. 2013. Conformational transition of membrane-associated terminally acylated HIV-1 Nef. Structure 21:1822-1833.
22. Jung J, Byeon I J, Ahn J, Gronenborn A M. 2011. Structure, dynamics, and Hck interaction of full-length HIV-1 Nef. Proteins 79:1609-1622.
23. Grzesiek S, Bax A, Clore G M, Gronenborn A M, Hu J S, Kaufman J, Palmer I, Stahl S J, Wingfield P T. 1996. The solution structure of HIV-1 Nef reveals an unexpected fold and permits delineation of the binding surface for the SH3 domain of Hck tyrosine protein kinase. Nature Struct Biol 3:340-345.
24. Singh P, Yadav G P, Gupta S, Tripathi A K, Ramachandran R, Tripathi R K. 2011. A novel dimer-tetramer transition captured by the crystal structure of the HIV-1 Nef. PLoS One 6:e26629.
25. Celniker G N, G.; Ashkenazy, H.; Glaser, F.; Martz, E.; Mayrose, I.; Pupko, T.; Ben-Tal, N. 2013. ConSurf: Using Evolutionary Data to Raise Testable Hypotheses about Protein Function. Isr J Chem 53:199-206.
26. Aiken C, Konner J, Landau N R, Lenburg M E, Trono D. 1994. Nef induces CD4 endocytosis: requirement for a critical dileucine motif in the membrane-proximal CD4 cytoplasmic domain. Cell 76:853-864.
27. Bentham M, Mazaleyrat S, Harris M. 2006. Role of myristoylation and N-terminal basic residues in membrane association of the human immunodeficiency virus type 1 Nef protein. J Gen Virol 87:563-571.
28. Cui H L, Grant A, Mukhamedova N, Pushkarsky T, Jennelle L, Dubrovsky L, Gaus K, Fitzgerald M L, Sviridov D, Bukrinsky M. 2012. HIV-1 Nef mobilizes lipid rafts in macrophages through a pathway that competes with ABCA1-dependent cholesterol efflux. J Lipid Res 53:696-708.
29. Ko T P, Liao C C, Ku W Y, Chak K F, Yuan H S. 1999. The crystal structure of the DNase domain of colicin E7 in complex with its inhibitor Im7 protein. Structure 7:91-102.
30. Kleanthous C, Kuhlmann U C, Pommer A J, Ferguson N, Radford S E, Moore G R, James R, Hemmings A M. 1999. Structural and mechanistic basis of immunity toward endonuclease colicins. Nature Struct Biol 6:243-252.
31. Wallis R, Moore G R, James R, Kleanthous C. 1995. Protein-protein interactions in colicin E9 DNase-immunity protein complexes. 1. Diffusion-controlled association and femtomolar binding for the cognate complex. Biochemistry 34:13743-13750.
32. Wallis R, Leung K Y, Pommer A J, Videler H, Moore G R, James R, Kleanthous C. 1995. Protein-protein interactions in colicin E9 DNase-immunity protein complexes. 2. Cognate and noncognate interactions that span the millimolar to femtomolar affinity range. Biochemistry 34:13751-13759.
33. Breuer S, Gerlach H, Kolaric B, Urbanke C, Opitz N, Geyer M. 2006. Biochemical indication for myristoylation-dependent conformational changes in HIV-1 Nef. Biochemistry. 45:2339-2349.
34. Trott O, Olson A J. 2010. AutoDock Vina: improving the speed and accuracy of docking with a new scoring function, efficient optimization, and multithreading. J Comp Chem 31:455-461.
35. Ramezani A, Dubrovsky L, Pushkarsky T, Sviridov D, Karandish S, Raj D S, Fitzgerald M L, Bukrinsky M. 2015. Stimulation of Liver X Receptor Has Potent Anti-HIV Effects in a Humanized Mouse Model of HIV Infection. J Pharmacol Exp Ther 354:376-383.
36. Morrow M P, Grant A, Mujawar Z, Dubrovsky L, Pushkarsky T, Kiselyeva Y, Jennelle L, Mukhamedova N, Remaley A T, Kashanchi F, Sviridov D, Bukrinsky M. 2010. Stimulation of the liver X receptor pathway inhibits HIV-1 replication via induction of ATP-binding cassette transporter A1. Mol Pharmacol 78:215-225.
37. Myerson M, Malvestutto C, Aberg J A. 2015. Management of lipid disorders in patients living with HIV. J Clin Pharmacol 55:957-974.
38. Wang T, Yi R, Green L A, Chelvanambi S, Seimetz M, Clauss M. 2015. Increased cardiovascular disease risk in the H W-positive population on ART: potential role of HIV-Nef and Tat. Cardiovasc Pathol 24:279-282.
39. Waheed A A, Freed E O. 2009. Lipids and membrane microdomains in HIV-1 replication. Virus Res 143:162-176.
40. Lee D, Kraus A, Prins D, Groenendyk J, Aubry I, Liu W X, Li H D, Julien O, Touret N, Sykes B D, Tremblay M L, Michalak M. 2015. UBC9-dependent association between calnexin and protein tyrosine phosphatase 1B (PTP1B) at the endoplasmic reticulum. J Biol Chem 290:5725-5738.
41. Gerlach H, Laumann V, Martens S, Becker C F, Goody R S, Geyer M. 2010. HIV-1 Nef membrane association depends on charge, curvature, composition and sequence. Nature Chem Biol 6:46-53.
42. Giese S I, Woerz I, Homann S, Tibroni N, Geyer M, Fackler O T. 2006. Specific and distinct determinants mediate membrane binding and lipid raft incorporation of HIV-1(SF2) Nef. Virology 355:175-191.
43. Hussain H, Al-Harrasi A, Al-Rawahi A, Green I R, Csuk R, Ahmed I, Shah A, Abbas G, Rehman N U, Ullah R. 2015. A fruitful decade from 2005 to 2014 for anthraquinone patents. Exp Opin Ther Pat 25:1053-1064.
44. Esposito F, Corona A, Zinzula L, Kharlamova T, Tramontano E. 2012. New anthraquinone derivatives as inhibitors of the HIV-1 reverse transcriptase-associated ribonuclease H function. Chemotherapy 58:299-307.
45. Molinari M, Eriksson K K, Calanca V, Galli C, Cresswell P, Michalak M, Helenius A. 2004. Contrasting functions of calreticulin and calnexin in glycoprotein folding and E R quality control. Mol Cell 13:125-135.
46. Danilczyk U G, Cohen-Doyle M F, Williams D B. 2000. Functional relationship between calreticulin, calnexin, and the endoplasmic reticulum luminal domain of calnexin. J Biol Chem 275:13089-13097.
47. Hebert D N, Zhang J X, Chen W, Foellmer B, Helenius A. 1997. The number and location of glycans on influenza hemagglutinin determine folding and association with calnexin and calreticulin. J Cell Biol 139:613-623.
48. Raney A, Kuo L S, Baugh L L, Foster J L, Garcia J V. 2005. Reconstitution and molecular analysis of an active human immunodeficiency virus type 1 Nef/p21-activated kinase 2 complex. J Virol 79:12732-12741.
49. Danilczyk U G, Williams D B. 2001. The lectin chaperone calnexin utilizes polypeptide-based interactions to associate with many of its substrates in vivo. J Biol Chem 276:25532-25540.
50. Hahn M, Borisova S, Schrag J D, Tessier D C, Zapun A, Tom R, Kamen A A, Bergeron J J, Thomas D Y, Cygler M. 1998. Identification and crystallization of a protease-resistant core of calnexin that retains biological activity. J Struct Biol 123:260-264.
51. Soding J, Biegert A, Lupas A N. 2005. The HHpred interactive server for protein homology detection and structure prediction. Nucleic Acids Res 33:W244-248.
52. Roy A, Kucukural A, Zhang Y. 2010. I-TASSER: a unified platform for automated protein structure and function prediction. Nat Protoc 5:725-738.
53. Pieper U, Webb B M, Dong G Q, Schneidman-Duhovny D, Fan H, Kim S J, Khuri N, Spill Y G, Weinkam P, Hammel M, Tainer J A, Nilges M, Sali A. 2014. ModBase, a database of annotated comparative protein structure models and associated resources. Nucleic Acids Res 42:D336-346.
54. Kelley L A, Sternberg M J. 2009. Protein structure prediction on the Web: a case study using the Phyre server. Nat Protoc 4:363-371.
55. Kallberg M, Wang H, Wang S, Peng J, Wang Z, Lu H, Xu J. 2012. Template-based protein structure modeling using the RaptorX web server. Nat Protoc 7:1511-1522.
56. Pawlowski M, Gajda M J, Matlak R, Bujnicki J M. 2008. MetaMQAP: a meta-server for the quality assessment of protein models. BMC Bioinformatics 9:403.
57. Berman H M, Westbrook J, Feng Z, Gilliland G, Bhat T N, Weissig H, Shindyalov I N, Bourne P E. 2000. The Protein Data Bank. Nucleic Acids Res 28:235-242.
58. The UniProt Consortium. 2014. UniProt: a hub for protein information. Nucleic Acids Res 43:D204-D212.
59. Fernandez-Fuentes N, Madrid-Aliste C J, Rai B K, Fajardo J E, Fiser A. 2007. M4T: a comparative protein structure modeling server. Nucleic Acids Res 35:W363-W368.
60. Biasini M, Bienert S, Waterhouse A, Arnold K, Studer G, Schmidt T, Kiefer F, Cassarino T G, Bertoni M, Bordoli L, Schwede T. 2014. SWISS-MODEL: modelling protein tertiary and quaternary structure using evolutionary information. Nucleic Acids Res 42:W252-W258.
61. Di Tommaso P, Moretti S, Xenarios I, Orobitg M, Montanyola A, Chang J M, Taly J F, Notredame C. 2011. T-Coffee: a web server for the multiple sequence alignment of protein and RNA sequences using structural information and homology extension. Nucleic Acids Res 39:W13-W17.
62. Kozakov D, Hall D R, Beglov D, Brenke R, Comeau S R, Shen Y, Li K, Zheng J, Vakili P, Paschalidis I C, Vajda S. 2010. Achieving reliability and high accuracy in automated protein docking: ClusPro, PIPER, SDU, and stability analysis in CAPRI rounds 13-19. Proteins 78:3124-3130.

63. Ritchie D W, Venkatraman V. 2010. Ultra-fast FFT protein docking on graphics processors. Bioinformatics 26:2398-2405.
64. Torchala M, Moal I H, Chaleil R A, Fernandez-Recio J, Bates P A. 2013. SwarmDock: a server for flexible protein-protein docking. Bioinformatics 29:807-809.
65. Pierce B G, Wiehe K, Hwang H, Kim B H, Vreven T, Weng Z. 2014. ZDOCK server: interactive docking prediction of protein-protein complexes and symmetric multimers. Bioinformatics 30:1771-1773.
66. Irwin J J, Shoichet B K. 2005. ZINC—a free database of commercially available compounds for virtual screening. J Chem Info Model 45:177-182.
67. Jubier-Maurin V, et al. 1999. Genetic Characterization of the nef Gene from Human Immunodeficiency Virus Type 1 Group M Strains Representing Genetic Subtypes A, B, C, E, F, G, and H. AIDS Research and Human Retroviruses. Volume 15, Number 1, pp. 23-32.

We claim:
1. A small molecule having the structure of Formula (II):

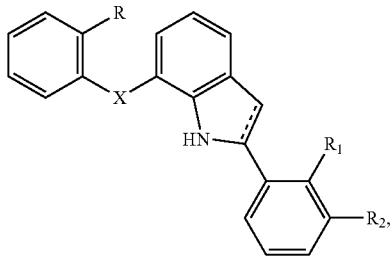

wherein:
R, $R_1$, and $R_2$ are independently selected from H, $CH_2OH$, COOH or $COOCH_3$; and
X is $CH_2$, NH, O, $NCH_3$, or $SO_2$,
wherein R is H, $R_1$ is H, $R_2$ is H, and X is $CH_2$ are not simultaneously satisfied.

2. A method for restoring or preserving cholesterol efflux in a cell infected with Human Immunodeficiency Virus (HIV) comprising delivering to the cell an effective amount of a composition or formulation comprising a small molecule of Formula (II) or an analog or derivative thereof:

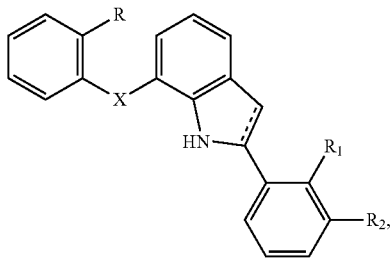

wherein:
R, $R_1$, and $R_2$ are independently selected from H, $CH_2OH$, COOH or $COOCH_3$; and
X is $CH_2$, NH, O, $NCH_3$, or $SO_2$,
wherein R is H, $R_1$ is H, $R_2$ is H, and X is $CH_2$ are not simultaneously satisfied.

3. The method of claim 2, wherein the small molecule binds to at least one amino acid residue on the Nef protein, wherein the at least one amino acid residue is selected from the group consisting of a lysine at amino acid position 4, a serine at amino acid position 6, a lysine at amino acid position 7, and a tyrosine at amino acid position 124.

4. The method of claim 2, wherein the small molecule binds to at least one amino acid residue on the Calnexin protein, wherein the at least one amino acid residue is selected from the group consisting of an aspartic acid at position 90, a glutamic acid at amino acid position 529, a glutamic acid at amino acid position 532, and a glutamic acid at amino acid position 533.

5. The method of claim 2, wherein preventing or decreasing the interaction between the Nef protein and the Calnexin protein results in at least partial restoration of ATP-Binding Cassette A1 (ABCA1) activity.

6. A method for treating or preventing atherosclerosis in a subject infected with HIV comprising administering to said subject an effective amount of a composition or formulation comprising a small molecule of Formula (II):

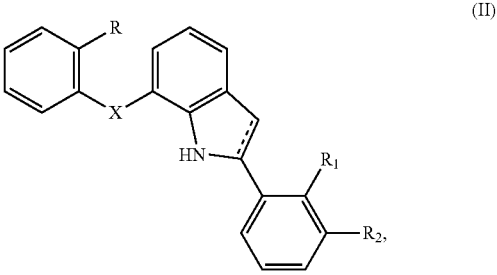

wherein R, $R_1$, and $R_2$ are independently selected from H, $CH_2OH$, COOH or $COOCH_3$; and
X is $CH_2$, NH, O, $NCH_3$, or $SO_2$; and
wherein the small molecule prevents or decreases an interaction between a Nef protein and a Calnexin protein, and
wherein R is H, $R_1$ is H, $R_2$ is H, and X is $CH_2$ are not simultaneously satisfied.

7. The method of claim 6, wherein the small molecule binds to at least one amino acid residue on the Nef protein, wherein the at least one amino acid residue is selected from the group consisting of a lysine at amino acid position 4, a serine at amino acid position 6, a lysine at amino acid position 7, and a tyrosine at amino acid position 124.

8. The method of claim 6, wherein the small molecule binds to at least one amino acid residue on the Calnexin protein, wherein the at least one amino acid residue is selected from the group consisting of an aspartic acid at position 90, a glutamic acid at amino acid position 529, a glutamic acid at amino acid position 532, and a glutamic acid at amino acid position 533.

9. The method of claim 6, wherein preventing or decreasing the interaction between the Nef protein and the Calnexin protein results in at least partial restoration of ATP-Binding Cassette A1 (ABCA1) activity.

* * * * *